(12) United States Patent
Garde et al.

(10) Patent No.: US 8,794,235 B2
(45) Date of Patent: Aug. 5, 2014

(54) SYSTEM AND METHOD FOR TREATING VENTILATORY INSTABILITY

(75) Inventors: Smita Garde, Irvine, CA (US); Stephen D. Pittman, Brookline, MA (US); Leonardo A. Baloa, Pittsburgh, PA (US); Stefanida Blake, Jamaica Plain, MA (US); Charles Thomas, Monroeville, PA (US); Manuel Laura, Pittsburgh, PA (US); Erik K. Witt, Murrysville, PA (US)

(73) Assignee: RIC Investments, LLC, Wilmington, DE (US)

( * ) Notice: Subject to any disclaimer, the term of this patent is extended or adjusted under 35 U.S.C. 154(b) by 1236 days.

(21) Appl. No.: 12/133,864

(22) Filed: Jun. 5, 2008

(65) Prior Publication Data

US 2008/0302364 A1 Dec. 11, 2008

Related U.S. Application Data

(60) Provisional application No. 60/933,752, filed on Jun. 8, 2007.

(51) Int. Cl.
*A61M 16/00* (2006.01)
*A62B 7/00* (2006.01)
*F16K 31/02* (2006.01)

(52) U.S. Cl.
USPC ............... 128/204.23; 128/204.22; 137/908

(58) Field of Classification Search
USPC ............ 128/204.23, 204.18, 204.21, 200.24, 128/204.22, 204.26–204.28, 128/205.23–205.24, 206.21, 128/206.28–206.29, 207.12, 128/207.14–207.18, 898; 137/908
See application file for complete search history.

(56) References Cited

U.S. PATENT DOCUMENTS

| | | | |
|---|---|---|---|
| 5,148,802 A | 9/1992 | Sanders et al. | |
| 5,245,995 A * | 9/1993 | Sullivan et al. | 128/204.23 |
| 5,313,937 A | 5/1994 | Zdrojkowski | |
| 5,433,193 A | 7/1995 | Sanders et al. | |
| 5,535,738 A * | 7/1996 | Estes et al. | 128/204.23 |
| 5,632,269 A | 5/1997 | Zdrojkowski | |
| 5,794,615 A | 8/1998 | Estes | |
| 5,803,065 A | 9/1998 | Zdrojkowski et al. | |
| 5,970,975 A * | 10/1999 | Estes et al. | 128/204.23 |
| 6,029,664 A | 2/2000 | Zdrojkowski et al. | |
| 6,042,550 A | 3/2000 | Haryadi et al. | |
| 6,098,622 A | 8/2000 | Nobile et al. | |
| 6,105,575 A | 8/2000 | Estes et al. | |
| 6,227,196 B1 | 5/2001 | Jaffe et al. | |

(Continued)

OTHER PUBLICATIONS

"align". Collins English Dictionary. 2000. http://www.credoreference.com/entry/hcengdict/align (Nov. 4, 2013).*

(Continued)

*Primary Examiner* — Tan-Uyen T Ho
*Assistant Examiner* — Mark K Han
(74) *Attorney, Agent, or Firm* — Michael W. Haas

(57) ABSTRACT

A therapy system adapted to treat a patient's ventilatory instability using a ventilatory therapy, a gas modulation therapy, or both. The algorithm implemented by the therapy system monitors the ventilatory instability, such as Cheyne Stokes Respiration (CSR), mixed apneas, CPAP emergent apneas, and complex sleep disordered breathing (CSDB) and treats the ventilatory instability. The algorithm also determine a reference point with respect to the ventilatory instability. The therapy delivery system initiate the treatment based on the reference point.

19 Claims, 18 Drawing Sheets

(56) References Cited

U.S. PATENT DOCUMENTS

| | | | |
|---|---|---|---|
| 6,269,269 B1 * | 7/2001 | Ottenhoff et al. | 607/42 |
| 6,360,741 B2 | 3/2002 | Truschel | |
| 6,408,848 B1 | 6/2002 | Feldman et al. | |
| 6,532,959 B1 * | 3/2003 | Berthon-Jones | 128/204.23 |
| 6,589,188 B1 | 7/2003 | Street et al. | |
| 6,609,517 B1 | 8/2003 | Estes et al. | |
| 6,626,175 B2 | 9/2003 | Jafari et al. | |
| 6,641,542 B2 * | 11/2003 | Cho et al. | 600/529 |
| 6,675,797 B1 * | 1/2004 | Berthon-Jones | 128/204.23 |
| 6,705,315 B2 * | 3/2004 | Sullivan et al. | 128/204.18 |
| 6,752,150 B1 * | 6/2004 | Remmers et al. | 128/204.18 |
| 6,752,151 B2 | 6/2004 | Hill | |
| 6,796,305 B1 * | 9/2004 | Banner et al. | 128/204.21 |
| 6,823,866 B2 | 11/2004 | Jafari et al. | |
| 6,839,581 B1 | 1/2005 | El-Solh et al. | |
| 6,920,875 B1 | 7/2005 | Hill et al. | |
| 6,932,084 B2 | 8/2005 | Estes et al. | |
| 6,948,497 B2 | 9/2005 | Zdrojkowski et al. | |
| 6,951,217 B2 * | 10/2005 | Berthon-Jones | 128/204.23 |
| 7,000,612 B2 | 2/2006 | Jafari et al. | |
| 7,011,091 B2 | 3/2006 | Hill et al. | |
| 7,025,730 B2 * | 4/2006 | Cho et al. | 600/529 |
| 7,073,501 B2 * | 7/2006 | Remmers et al. | 128/204.18 |
| 7,077,132 B2 * | 7/2006 | Berthon-Jones | 128/204.23 |
| 7,100,607 B2 | 9/2006 | Zdrojkowski et al. | |
| 7,160,252 B2 | 1/2007 | Cho et al. | |
| 7,296,573 B2 * | 11/2007 | Estes et al. | 128/204.23 |
| 7,438,686 B2 * | 10/2008 | Cho et al. | 600/484 |
| 7,469,697 B2 * | 12/2008 | Lee et al. | 128/200.24 |
| 7,766,840 B2 * | 8/2010 | Kwok et al. | 600/508 |
| 7,810,497 B2 * | 10/2010 | Pittman et al. | 128/204.23 |
| 2004/0144383 A1 | 7/2004 | Thomas et al. | |
| 2005/0039745 A1 * | 2/2005 | Stahmann et al. | 128/204.18 |
| 2005/0109339 A1 * | 5/2005 | Stahmann et al. | 128/204.18 |
| 2005/0274381 A1 * | 12/2005 | Deane et al. | 128/204.23 |
| 2006/0070624 A1 | 4/2006 | Kane et al. | |
| 2009/0308394 A1 * | 12/2009 | Levi | 128/204.23 |
| 2013/0197321 A1 * | 8/2013 | Wilson | 600/301 |

OTHER PUBLICATIONS

U.S. Appl. No. 60/784,127, Pittman et al.

Thomas, R. et al. "Low-Concentration Carbon Dioxide is an Effective Adjunct to Positive Airway Pressure in the Treatment of Refractory Mixed Central and Obstructive Sleep-Disordered Breathing", SLEEP, vol. 28, No. 1, 2005, pp. 69-77.

Khayat, R. et al. "Cardiorespiratory Effects of Added Dead Space in Patients with Heart Failure and Central Sleep Apnea", American College of Chest Physicians, 2003;123, pp. 1551-1560.

* cited by examiner

SYSTEM AND METHOD FOR TREATING VENTILATORY INSTABILITY

CROSS-REFERENCE TO RELATED APPLICATIONS

This application claims priority under 35 U.S.C. §119(e) from provisional U.S. patent application No. 60/933,752, filed Jun. 8, 2007, the contents of which are incorporated herein by reference.

BACKGROUND OF THE INVENTION

1. Field of the Invention

The present invention pertains to a system and method of treating ventilatory instability using a ventilatory therapy, a gas modulation therapy, or a combination thereof, and, in particular, to a system and method for treating ventilatory control instability, such as Cheyne Stokes Respiration (CSR), mixed (obstructive and central) apneas, CPAP emergent apneas, complex sleep disordered breathing (CSDB), drug induced central apneas, and high-altitude central apneas, in a dynamic, adaptive fashion.

2. Description of the Related Art

Cheyne-Stokes Respiration (CSR) is one example of ventilatory instability. It is defined as a cyclic alternating pattern of hyperventilation (increased ventilatory drive) and hypoventilation (decreased ventilatory drive). Such recurring cyclic respiratory instability patterns are predominantly experienced by patients suffering from heart failure. The cyclic changes in ventilation in these patients are caused by the instability of the ventilatory control system. This instability is believed to be caused by a high loop gain of the ventilatory feedback control system, an increased chemosensitivity, and longer circulatory delay in the chemoreceptor response.

The instability of the ventilatory control is also experienced in non-heart failure patients with mixed apneas and CPAP emergent central sleep apneas. Mixed apnea is the combination of both central apneas and obstructive apneas. The term apnea, or apneic events, for the purposes of this document includes hypopneas. CPAP emergent central sleep apnea occurs when an upper airway obstruction is eliminated with PAP therapy, unmasking central sleep apneas. These conditions have been treated conventionally using a positive airway pressure (PAP) therapy, such as continuous positive airway pressure (CPAP) therapy. In such cases, the use of PAP therapy leads to cyclic patterns of increased and decreased ventilatory drive and central apneas during the night that cannot be treated with an increase in the CPAP pressure.

One of the treatment options for treating CSR includes using a PAP based servo-ventilation device that delivers a high pressure during inhalation and a lower pressure during exhalation to ventilate or help ventilate the patient. This type of therapy focuses on the periods where the patient experiences reduced ventilation to try to offset this ventilatory decrease. An apparatus for the treatment of CSR is also disclosed in the U.S. patent application Ser. No. 11/235,520 (publication no. US 2006 0070624 A1) ("the '520 application"), the contents of which is hereby incorporated by reference in its entirety. A ventilatory assistance method for treatment is further disclosed in the U.S. Pat. No. 7,077,132 ("the '132 patent"), the contents of which is hereby incorporated by reference in its entirety.

One possible therapy for treating CSR is to attempt to control the carbon dioxide ($CO_2$) gas that the patient receives. This can be done in a variety of ways, such as by providing additional dead space in the patient breathing circuit to cause carbon dioxide ($CO_2$) rebreathing. $CO_2$ can also be provided to the patient by adding $CO_2$ gas from an external supply to the patient breathing circuit. These types of gas modulation therapies in which the $CO_2$ levels received by the patient are regulated, stabilize the patient's ventilatory control system by decreasing the loop gain of that control system.

An increased level of $CO_2$ in the patient's breathing circuit can also be achieved by allowing $CO_2$ rebreathing through the manipulation the leak of exhaled air through an exhalation port on the patient interface. An apparatus for reducing central sleep apnea using these gas is disclosed in the U.S. Pat. No. 7,073,501 ("the '501 patent"), the content of which is hereby incorporated by reference in its entirety.

SUMMARY OF THE INVENTION

The present inventors recognized that in implementing the above-described conventional ventilation-based therapies and gas modulation-based therapies to treat sleep disordered breathing already described above, for example, involves providing that therapy continuously, with a fixed or preset level of intervention. The present inventors recognized that ventilatory instability can be better treated using a more adaptive treatment approach. The therapy algorithm described herein and used by the therapy system of the present invention uses a treatment approach that is based on the information about the extent of the ventilatory instability in the ventilatory control system and the dynamics of ventilatory cyclic behavior.

Based on this approach, the therapy algorithm of the present invention, in one exemplary embodiment, is a combination of a ventilatory therapy and a gas modulation therapy in that the therapy is implemented in a PAP device that is also adapted to deliver a gas modulation therapy. In a first embodiment, the gas modulation therapy is the primary control to treat the ventilatory instability. For example, a brief duration a gas modulation therapy, such as $CO_2$ rebreathing therapy is provided to the patient at an appropriate time in the respiratory cycle. This can be done alone or in combination with the ventilatory therapy. For example, the ventilatory therapy can be controlled so as to cause the patient to rebreathe some or all of his or he exhaled $CO_2$. In a second embodiment, the ventilatory therapy is the primary control to treat the ventilatory instability. For example, brief pulses of increased positive PAP pressure are provided to the patient at an appropriate time in the respiratory cycle. This can be done alone or in combination with a gas modulation therapy. The present invention contemplates that the gas modulation therapy can include control of gasses other than $CO_2$ delivered to the patient, such as control the amount of oxygen ($O_2$).

The present invention further contemplates therapy systems and algorithms for an adaptive and dynamic control for the ventilatory therapy and/or the gas modulation therapy, as well as any other interventions suitable for use in ventilatory stabilization. The present invention contemplates determining the characteristic dynamics of the underlying ventilatory instability and controlling the therapy intervention (ventilatory therapy, gas modulation therapy, or both) based on characteristic dynamics of the underlying ventilatory instability.

The present invention still also describes alternative systems and methods for providing an adaptive gas modulation therapy and/or ventilatory therapy to treat ventilatory instability. A characteristic feature of ventilatory instability disorders is the cyclic changes in the breathing pattern that represent the instability in the underlying ventilatory control system. The system described herein delivers therapy that use both a ventilatory and gas modulation therapy and alter these therapies individually or together to overcome this instability. A feature of this therapy algorithm is that the therapy intervention is applied in a dynamic manner, at certain instances of time in the respiratory cycle, so as to counteract the cyclic decrease in ventilatory drive. The activation of therapy is aligned to a reference point in the cyclic breathing pattern, which corresponds to the change from an increasing to a decreasing ventilatory drive. It should be noted that the reference point need not be a fixed morphological marker. The term "reference point" implies any descriptor of an oscillating system or repetitive physiological waveform or rhythm that could serve as a reference for triggering therapy. This includes a time difference, phase shift, mathematical descriptions of a curve such as curve fitting or frequency domain parameters, etc. The level of therapy is controlled continuously, not fixed or preset, so as to stabilize the ventilatory control system and overcome the cyclic breathing pattern in an optimal fashion.

In an exemplary embodiment of the present invention, the therapy system is based on a positive airway pressure platform and combines different modes of ventilatory therapies and gas modulation therapies with auto-titration algorithms and comfort enhancement features, such as controlling the pressure based on patient flow or respiratory effort, providing a bi-level pressure that varies in synchronization with the patient's respiratory cycle so that a higher pressure is delivered during inspiration than during expiration, to maximize the effectiveness of the treatment as well as the comfort to the patient.

The therapy system of one exemplary embodiment includes (1) a device or module capable of detecting cyclic breathing patterns and obstructive and central apnea events, (2) a device or module capable of providing an adaptive control of a ventilatory and/or gas modulation therapy, i.e., provides increases and decreases in therapy levels that are aligned to cyclic changes, and (3) a therapy delivery system that comprises of one or more combinations of ventilatory therapies and gas modulation therapies, such as $CO_2$ rebreathing through variable deadspace or a $CO_2$ supply, $O_2$ gas delivery from an external supply, dynamic positive airway pressure changes, or any combination thereof.

The therapy system continuously monitors one or more characteristics of the patient, for example, through changes in patient's breathing pattern, changes in patient's $CO_2$ and $O_2$ levels, changes in the respiratory effort, flow, pressure, or respiratory physiological parameter, or any combination thereof. The detector module in the therapy system performs the following:

a) detection and pre-detection or prediction of the peak of the cyclic changes in the ventilatory drive as the reference point for therapy activation, which may include the determination of cycle length or frequency, b) computation of one or more indices to indicate the level of cyclic instability; these indices are calculated from one or more patient signals monitored in the therapy device, and c) detection and classification of apneic events as obstructive and central apneas.

The present invention also contemplates determining intra-breath parameters, such as inspiration and expiration times, or events that occur in the timescale of a single breath.

The therapy system activates and deactivates the therapy system dynamically based on the detection of instability (e.g. increase $CO_2$ and decrease $CO_2$ breathing). A controller module in the therapy system uses the information about the cyclic changes in the breathing patterns and other patient signals that indicate the changes in the ventilatory drive. The controller module monitors (i) the increase and decrease in the level of the ventilatory drive and (ii) the delay in the effect of these changes, and activates therapy that counters the effect of a decreasing ventilatory drive.

The therapy system adaptively adjusts the time and duration of ventilatory therapy, the gas modulation therapy or both during the cyclic changes based on the cycle reference point and the extent of instability, and the apneic events (obstructive or central apneas). In an exemplary embodiment, the maximum duration of therapy for each activation is equal to the number of breaths in the crescendo to decrescendo of the cycle.

In one implementation, the controller module activates the therapy level that is fixed, or, in another implementation, the therapy level is variable and is proportional to the extent of instability. In yet another implementation, the controller module updates its parameters and model using adaptive feedback and learning schemes. In yet another implementation, the controller may monitor altitude of the device (by sensor input, manually by the user, or any other suitable technique/method) to further adjust the to timing and control of the therapy due to the effects of altitude on chemoreceptor sensitivity.

An actuator module in the therapy system uses the therapy activation to control the ventilatory and/or gas modulation therapy. For example, the actuator module can provide signals that control a valve, a diaphragm, a motor, or any other components of PAP or gas delivery system in the therapy module. In one exemplary embodiment, the present invention contemplates providing $CO_2$ rebreathing by activating a valve to partially or fully close the exhalation ports on patient interface. The actuator module also implements the dynamic control of gas delivery system for breathing $CO_2$ and/or $O_2$ gas. A bank of valves is controlled by the actuator module to implement addition of variable or adaptive deadspace in the patient breathing circuit. The actuator module in the therapy system supports a one or more hardware control implementations for delivery of therapy.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

I. Overview

The present invention describes a therapy system that is capable of providing a ventilatory therapy, a gas modulation therapy, or both to a patient to treat a ventilatory instability, such as CSR. In an exemplary embodiment, the therapy system is a positive airway pressure (PAP) system that also includes components for providing a gas modulation therapy (e.g. $CO_2$ rebreathing/external $CO_2$ or $O_2$ delivery, etc.) for the treatment of the ventilatory control instability, such CSR, mixed apneas, CPAP emergent apneas, and complex sleep disordered breathing (CSDB). The present invention contemplates controlling the PAP device and/or additional hardware implemented in the PAP based device, to deliver a gas modulation therapy, ventilatory therapy, or combination therapy, with other applicable therapies, such as gas mixture (e.g. $CO_2$ and $O_2$, or variable deadspace or positive pressure pulses etc.) to treat these conditions.

This invention also describes an algorithm to detect instability in ventilatory control system (e.g. CSDB and CSR) and to control and treatment therapy in an optimal manner to treat the ventilatory instability. A feature of the therapy algorithm implemented by the present invention is that the therapy intervention is applied in a dynamic manner, at certain instance of time in the respiratory cycle, that counteracts with the cyclic decrease in ventilatory drive. In an exemplary embodiment, the activation of therapy is aligned to a reference point in the cyclic breathing pattern that corresponds to the change from an increasing to a decreasing ventilatory drive. The level of therapy or $CO_2$ breathing is controlled continuously to stabilize the ventilatory control system and overcome the cyclic breathing pattern.

Figure 1A:
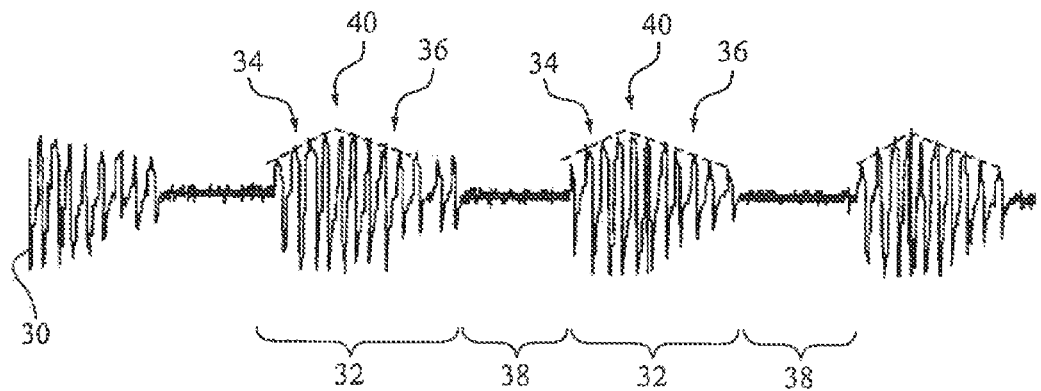
FIG. 1A is a graph showing a typical CSR breathing pattern.

The cyclic changes in a CSR cycle are described by repetitive crescendo-decrescendo-hypopnea changes or repetitive crescendo-decrescendo-apnea changes. FIG. 1A illustrates a typical flow waveform 30 or a patient experiencing a CSR breathing pattern, where each CSR cycle 32 includes a crescendo phase 34 lasting several breaths and a decrescendo phase 36 also lasting several breaths, followed by an apnea phase 38. This ventilatory instability is believed to be caused by peripheral/central chemoreceptor imbalance and a highly sensitive apneic threshold. A chemoreceptor is a sensor for the levels of $CO_2$ and $O_2$ in the body. The brain receives the signal from the chemoreceptors and responds by increasing the respiratory drive for an increased level of $CO_2$ and by decreasing the respiratory drive for a decreased level of $CO_2$ or an increased level of $O_2$ in the body. Approximately 70-80% of the ventilatory response to changes in $CO_2$ levels is mediated by the central chemoreceptors and remaining 20%-30% is mediated by the peripheral chemoreceptors. The central chemoreceptor response time is ~2-5 minutes and peripheral chemoreceptor response time is ~20-30 seconds. Hence, the duration of the cyclic changes indicate the increased role of peripheral chemoreceptors and circulatory delay in causing the instability in ventilatory drive.

Figure 1B:
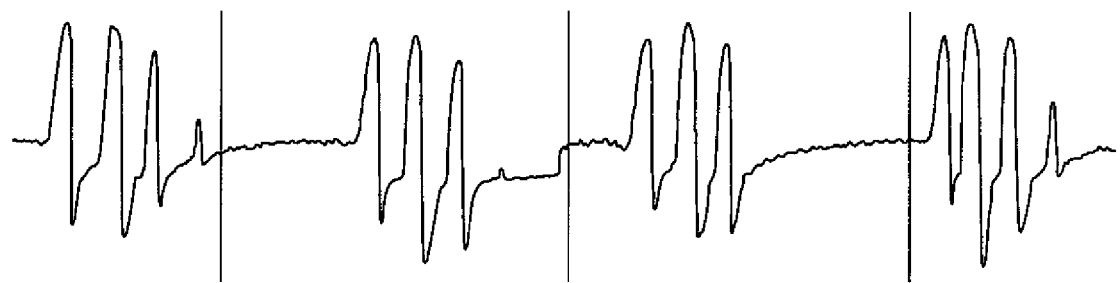
FIG. 1B is a graph showing a typical CPAP emergent central apnea pattern.
Figure 1C:
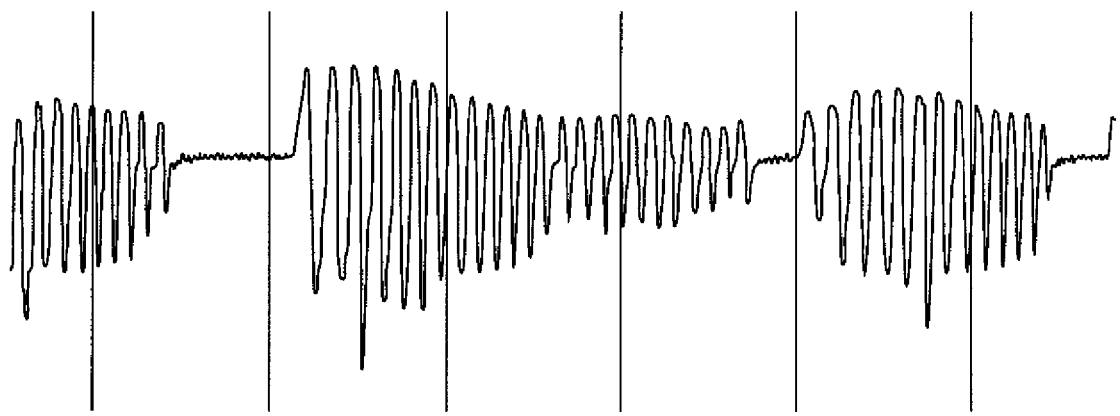
FIG. 1C is a graph showing a typical drug-induced apnea pattern.

FIG. 1B is a graph of patient flow showing a typical flow CPAP emergent central apnea pattern. FIG. 1C is a graph of patient flow showing a typical drug-induced apnea pattern. The conditions are further examples of ventilatory instability that is capable of being detected and treated by the present invention.

The system and method of the present invention provides a treatment that is based on the response time of peripheral chemoreceptors (faster response) and central chemoreceptors (slower response) to treat the ventilatory instability. For example, the present invention contemplates providing a therapy (ventilatory and/or gas modulation) that incorporates the response time of the chemoreceptors and circulatory delay to stabilize the feedback control loop by providing brief duration therapies (e.g., therapies that last for a few breaths) initiated at proper time in the feedback control loop timing.

In an exemplary embodiment, the timing of the treatment therapy is aligned to a reference point in the cyclic instability that is detected by the algorithm. For example, FIG. 1D shown a reference point 40 as being a peak between the crescendo phase 34 and decrescendo phase 36 of the CRS cycle. The therapy intervention is applied to counter the change (decrease or increase) in ventilatory drive and stabilize the feedback loop for ventilatory control. By incorporating the concept of response delay, primarily for the faster responding peripheral chemoreceptors, this approach will drive the ventilatory control system towards stability.

The term "reference point" implies any descriptor of an oscillating system or repetitive physiological waveform or rhythm that could serve as a reference for triggering therapy. This includes a time difference, phase shift, mathematical descriptions of a curve such as curve fitting or frequency domain parameters, etc.

In summary, the present invention describes an algorithm for an adaptive and dynamic control for a treatment therapy, i.e., ventilatory therapy, gas modulation therapy, or a combination thereof. The gas modulation therapy can be any therapy that controls one or more gasses delivered to the patient, such as $CO_2$ rebreathing, $CO_2$ breathing, $O_2$ therapy. The ventilatory therapy, gas modulation therapy, or a combination thereof can also be used with any other ventilatory stabilization intervention, such as the use of external pressures or medications. Adapted and dynamic control of the treatment therapy is achieved by extracting information about the extent or level of ventilatory instability and the cycle time that relates to the response time of the chemoreceptors and circulatory delay in ventilatory control loop and using this information in a feedback fashion to control the therapy treatment.

II. Therapy System

Figure 2:
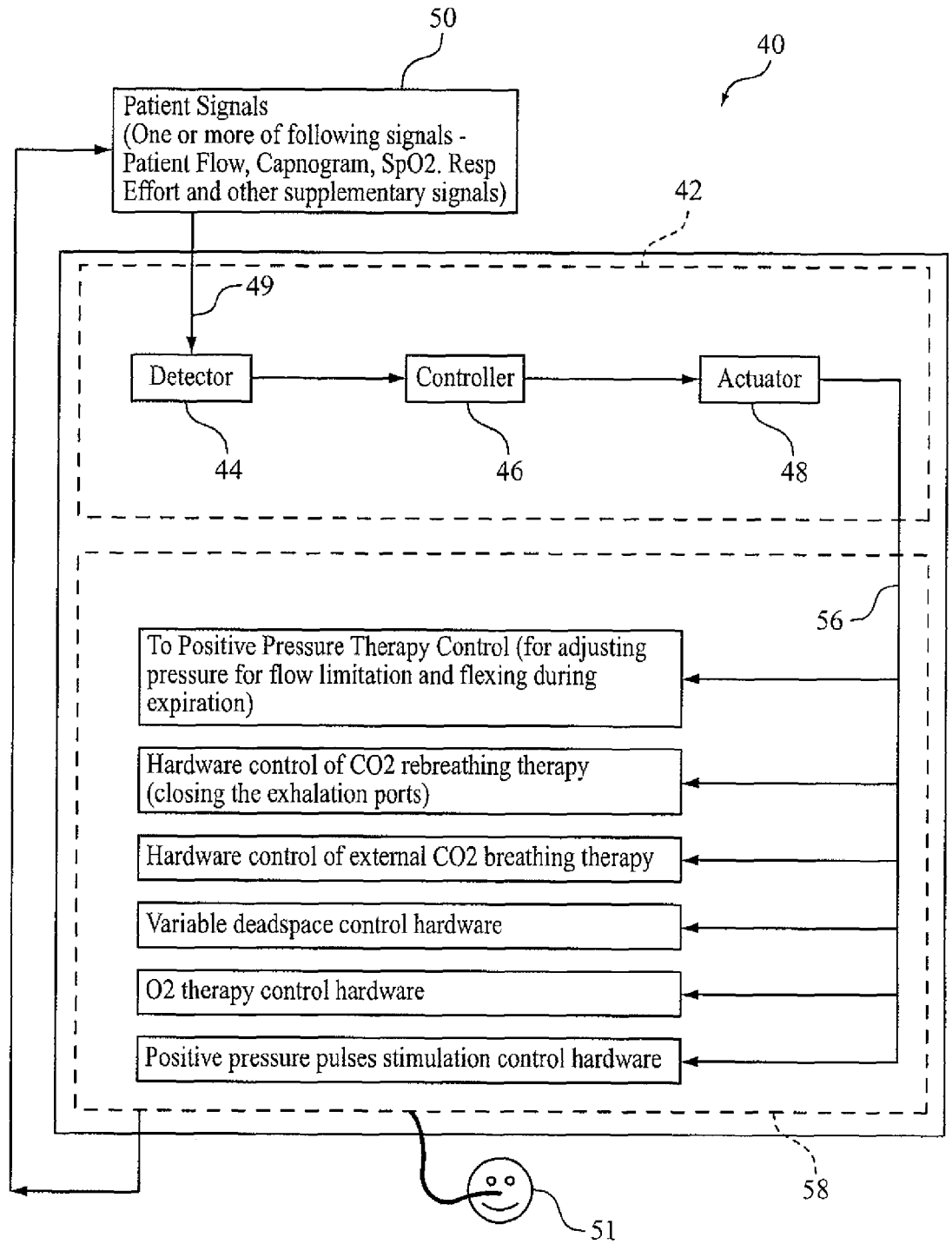
FIG. 2 is a schematic diagram of a system that implements a therapy algorithm according to the principles of the present invention.

FIG. 2 schematically illustrates a therapy system 40 that implements a dynamic treatment therapy, such as ventilatory control, gas modulation, or both according to the principles of the present invention. Therapy system 40 includes an implementation module 42 and a therapy module 58. Implementation module 42 includes a ventilatory drive instability detector ("detector") module 44, a controller module 46, and an actuator 48. As described in greater detail below, detector module 44 derives various indices for ventilatory instability from one or more patient signals 49 provided by one or more sensors 50. Ventilatory drive instability detector module 44 also determines, for example, reference point 40 in a CSR cycle. Sensors 50 include any sensors suited to detect the physiologic condition of the patient, such as flow, volume, pressure, temperature, capnography, $SpO_2$, $O_2$, and respiratory effort. Sensors 50 can be included in implementation module 40, therapy module 58, or they can be provided externally to these modules.

Controller module 46 controls the activation, deactivation, and level of therapy that is aligned to the cyclic changes in ventilatory drive. Actuator module 48 controls one or more of the components of therapy module 58, which is the portion of the therapy system that provides the actual therapy (ventilatory and/or gas modulation) to a patient 51. For example, the present invention contemplates that actuator module 48 provides actuator signals 56 for controlling hardware in therapy module 58, such as a valve, diaphragm, motor speed, servomotor, to implement the therapy.

Various therapy modes are supported by the algorithm of the present invention through actuator module 48. That is, the present invention contemplates that therapy module 58 include hardware for providing a variety to therapies to treat ventilatory instability. For example, FIG. 2 illustrates six possible, but not exclusive, therapy modes that can be applied alone or in any combination by therapy module 58 through the signals or other control techniques provided by actuator module 48.

A. Ventilatory Drive Instability Detector Module

Figure 3:
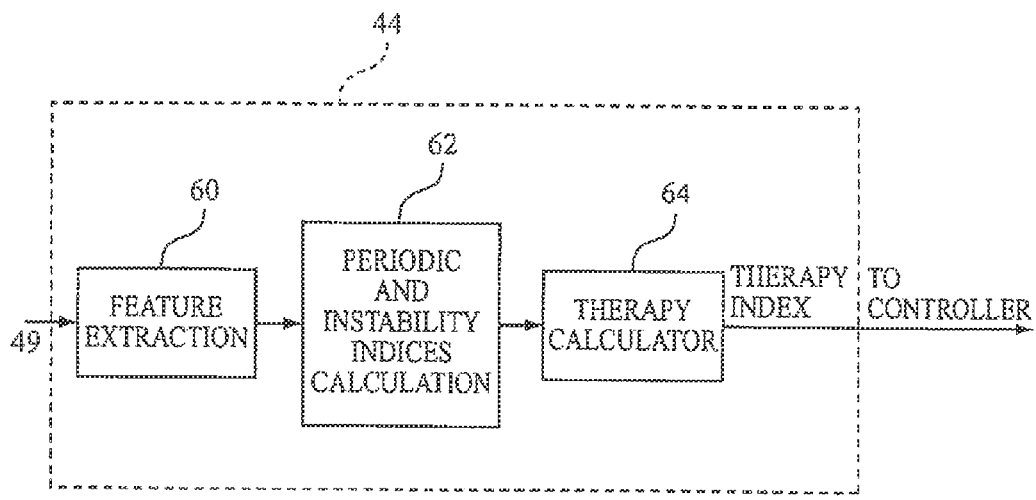
FIG. 3 is a block diagram of detector module according to the principles of the present invention.

One function of ventilatory drive instability detector module 44 is to derive information about the extent of the ventilatory instability and the dynamics of the ventilatory instability in the patient's ventilatory feedback control system. Detector module 44, as shown in greater detail in FIG. 3, derives indices based on one or more patient signal(s) 49 that include—flow, respiratory effort, photoplethysmogram and oxygen desaturation, capnogram information, $EtCO_2$, and patient pressure. In an exemplary embodiment, detector module 44 includes the following:

a) a feature extraction module 60 that extracts one or more features from patient signals 49, b) a calculation module 62 that determines indices that relate to the time of reference point in the ventilatory cycle, level of instability, and periodicity of the cyclic behavior, and c) a therapy index module 64 that determines indices and performs therapy index calculations for different controller implementations.

Figure 4:
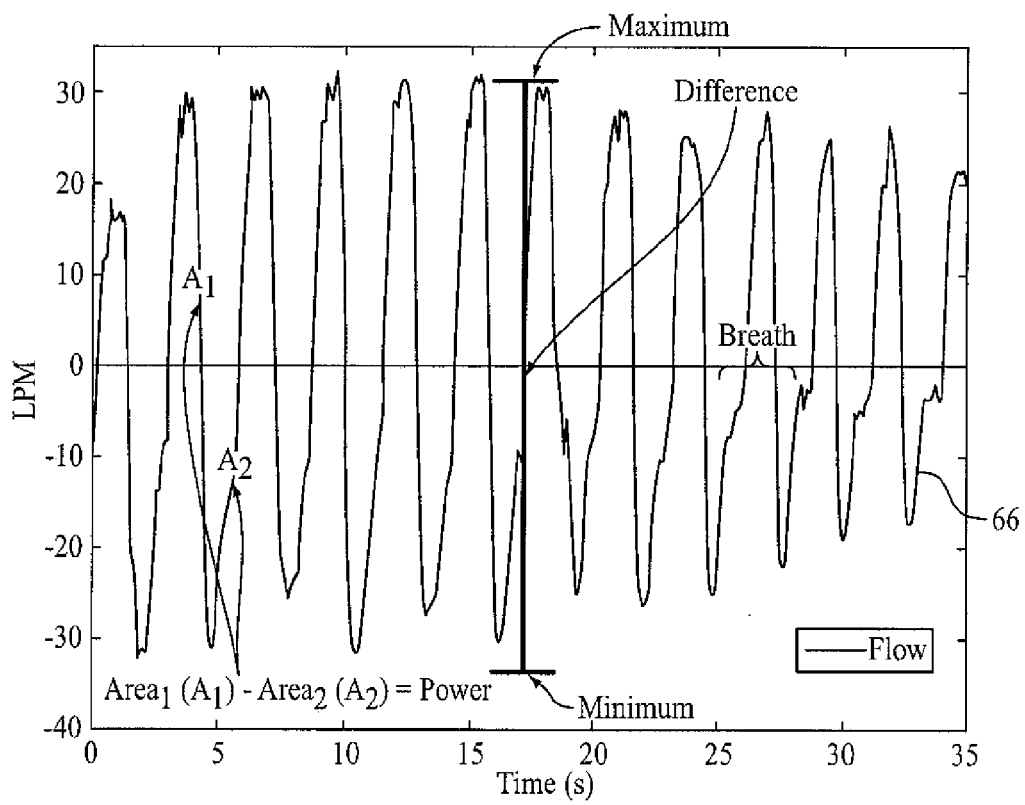
FIG. 4 is a graph of a flow waveform showing examples of patient flow features that can be used in the detector implementation.

FIG. 4 is a flow waveform 66 that illustrates various characteristics or parameters that can be derived from this flow waveform by detector module 44. The following exemplary parameters are shown as being obtained from waveform 66: Inspiratory and Expiratory Volumes ($Area_1$ and $Area_2$), Power ($Area_1 - Area_2$), Peak flows (Max and Min), Delta Peak (Difference between peak max and peak min, and breath durations. Of course, this list of parameters is not intended to be exhaustive, but merely illustrative, because the amount and type of information that can be determined and/or derived from the flow signal, for example, is quite large.

B. Controller Module

Figure 8:
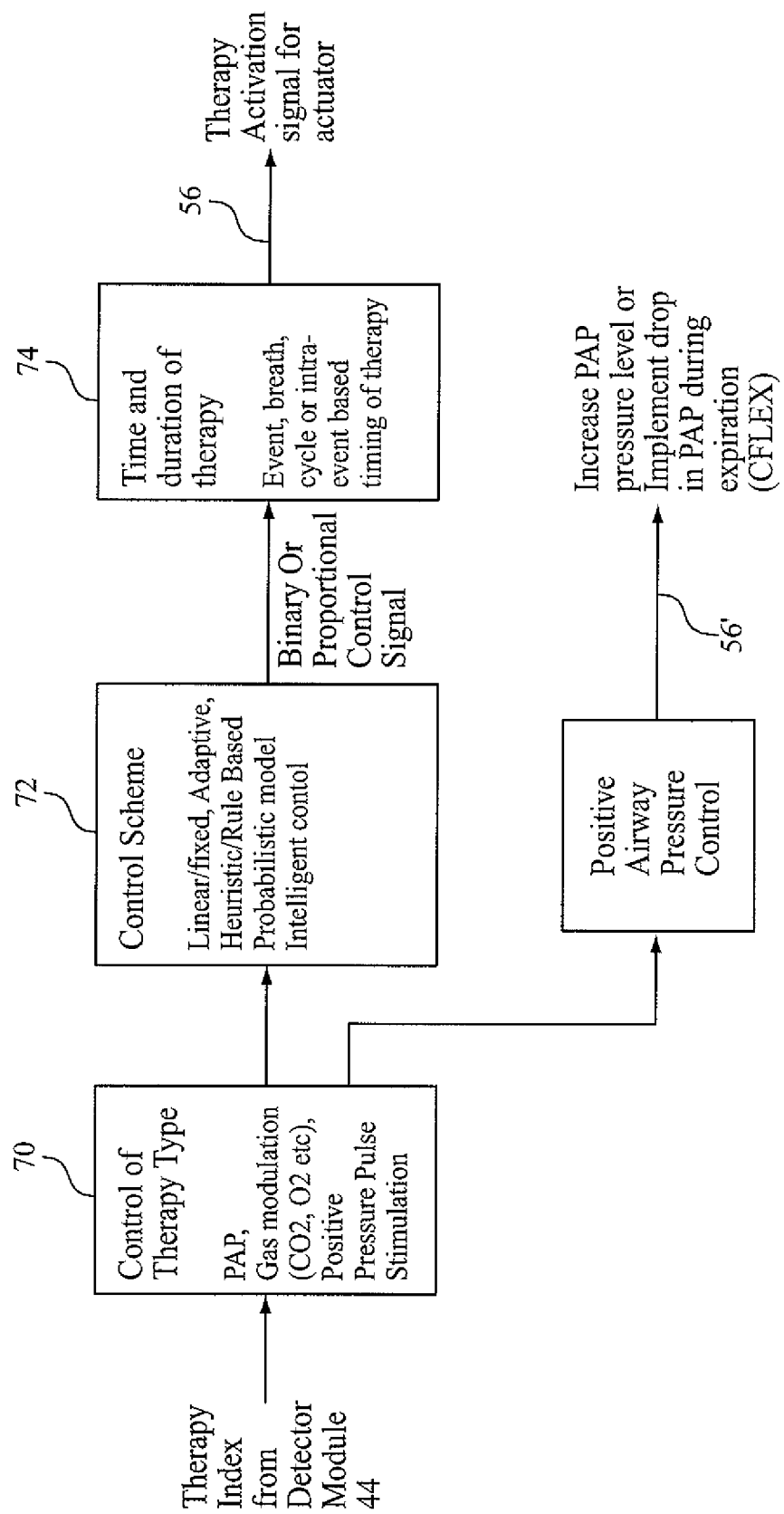
FIG. 8 is a block diagraph of a controller module.
Figure 9:
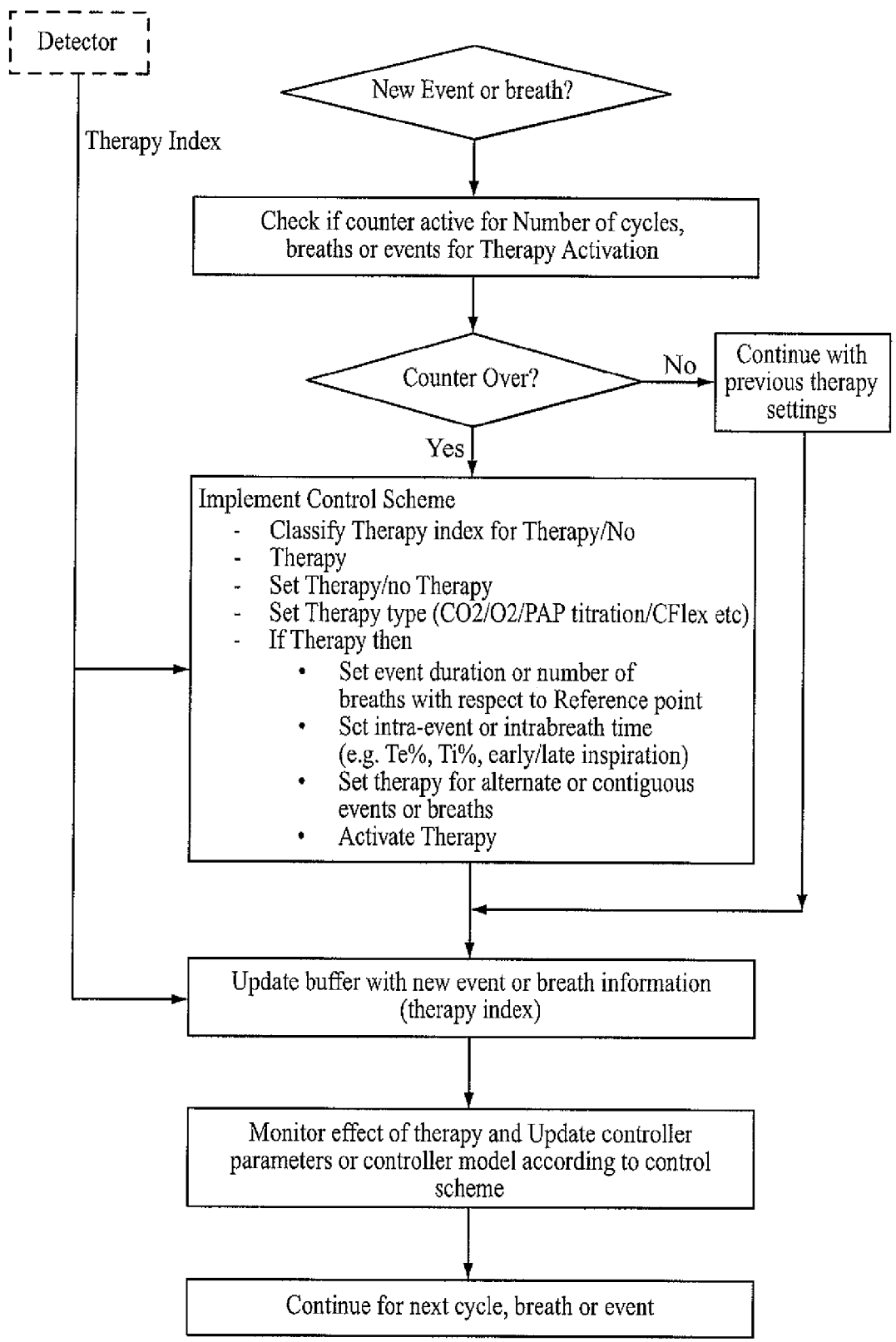
FIG. 9 is a flowchart illustrating the process carried out by the controller according to the principles of the present invention.

Controller module 46 implements a control algorithm, an example of which is illustrated in FIG. 8 in block diagram form. FIG. 9 is a flowchart illustrating the process carried out by the controller module according to the principles of the present invention algorithm. The present invention contemplates, for example, that controller module 46 includes the following tasks/functions:

a) control of the therapy type 70, such as:
  (i) therapy duration/level and timing for $CO_2$ rebreathing, and/or external $CO_2$ breathing, and/or $O_2$ breathing, and/or variable deadspace,
  (ii) proportional positive airway pressure (PPAP) therapy pressure control,
  (iii) bi-level pressure control, and/or
  (iv) positive pressure pulses.

b) implementation of control schemes 72, such as:
  (i) binary (on/off or fixed control,
  (ii) proportional,
  (iii) adaptive,
  (iv) heuristics/rule-based,
  (v) fuzzy-based, and/or
  (vi) memory based (learning) intelligent control.

c) control of the time and duration of the therapy 74, such as:
  (i) activation of therapy over multiple breaths with respect to the cycle reference point,
  (ii) intra-breath duration of the therapy (partial or full, or early/late inspiration),
  (iii) alternate breaths or specific breath type intervention, and/or
  (iv) alternating cycles or skipping a fixed number or varying number of cycles.

C. Actuator Module

Based on the therapy activation, actuator module 48 generates actuator signals 56 for controlling the hardware need to provide the different therapy options. The actuator signals are used to control various types of valves, actuators, diaphragms, servo-controls and may include or more signals. Examples of actuator signals include, but are not limited to, binary (on/off) signals, sawtooth signals, pulse width modulated waveforms (PWM), Frequency modulated or frequency shift keying signals. Details of the detector module, the controller module, and the actuator module are given below, each in separate section.

III. Ventilatory Drive Instability Detector Module

Ventilatory drive instability detector module 44 implements the detection of cyclic, periodic, or quasi-periodic instability in the patient's ventilatory drive. As noted above, detector module 44 extracts one or more features from one or more patient signals and derives various indices that characterize the patient's ventilatory control system and flow limitation due to an increased upper airway resistance. The detector module classifies a therapy index that is used in the controller module implementation. Referring again to FIG. 3, and as noted briefly above, detector module 44 includes feature extraction module 60, calculation module 62, and therapy index calculation module 64 that perform the following functions:

a) feature extraction from patient signal(s) 49,
  b) calculation of instability, periodicity, and flow limitation indices, and
  c) ventilatory drive instability therapy index calculation for different controller implementations.

The detector module uses one or more patient signals that exhibit similar cyclic changes that are correlated to the cyclic ventilatory control instability. The present implementation of the therapy algorithm in a PAP device can use one or more of the following physiological signals and parameters, but is not limited to:

a) flow,
  b) volume and minute ventilation,
  c) respiratory effort,
  d) capnogram and/or end tidal $CO_2$, and
  e) $SpO_2$ and/or photoplethysmogram.

In other implementations of the detector module, other physiological signals can be included that will contribute to the identification of ventilatory drive instability.

A. Feature Extraction from Patient Signal(s)

Feature extraction module 60 in detector module 44 includes implements a feature extraction technique using a number of physiological signals that may be monitored in the therapy module, externally to the therapy module, or both. In this implementation, one or more features can be used. Examples of such features include but are not limited to, the following:

a) maximum value of original and detrended signal,
  b) minimum value original and detrended signal,
  c) difference between Maximum and Minimum value,
  d) normalized difference between Maximum and Minimum value,
  e) mean value,
  f) standard deviation,
  g) variance,
  h) derivative,
  i) integral,
  j) power,
  k) frequency,
  l) event, breath or cycle period, or
  m) any other morphological features.

These features can be extracted for different time-scales and events, such as:

a) breath by breath,
  b) second-by-second or multiple seconds,
  c) during each respiratory cycle, or
  d) any combination of (a)-(c).

Examples of some features that can be calculated from a patient flow signal for breath-by breath analysis are shown in FIG. 4, as described above.

B. Instability and Periodicity Indices

Figure 5:
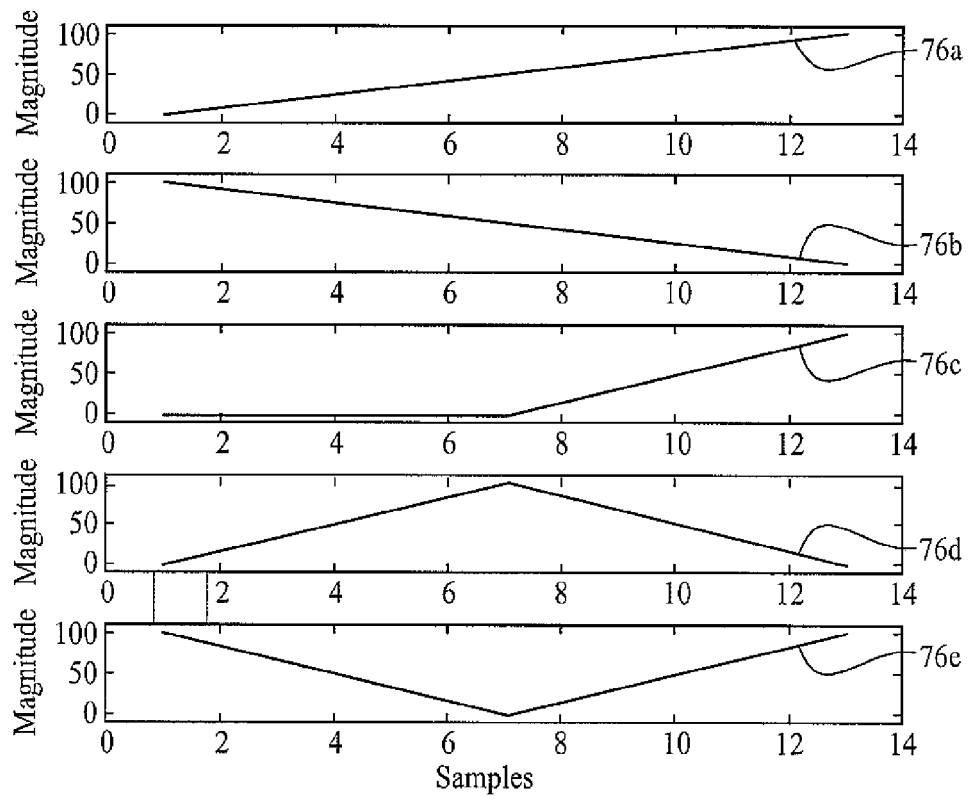
FIG. 5 are graphs of examples of templates used for the calculation of a correlation index.

Calculation module 62 in detector module 44 calculates various indices from the features extracted from the patient signals via feature extraction module 60. These indices are calculated to provide an estimate of the instability and the cyclic characteristic of the instability in the ventilatory drive. There are many ways to calculate indices that represent characteristics of the ventilatory instability. The present invention contemplates that calculation module 62 calculates one or more of following indices that represent characteristics of the ventilatory instability:

Correlation Index (CI): This index is calculated to get the peak of the cyclic, periodic, or quasi-periodic characteristics of the patient signal. This index compares the analyzed signal to a template to determine the cyclic behavior. The template varies in shape and length according to the signal being analyzed. FIG. 5 depicts examples of various templates 76a-76e having different shapes and all with a sample length of thirteen samples. The correlation index is calculated by sliding the template signal over each sample of the extracted features. It is to be understood that other template shapes and/or other number of samples can be used to determine the correlation index.

Modulation Index (MDI): This index determines the extent or depth of the instability in a patient signal. The modulation index is calculated as:

$$MDI(i) = \frac{f(i) - f(i-K)}{f(i)}, \quad \text{(Eq. 1)}$$

where f(i) is the current value of the feature used for analysis, and K is factor that is related to the cycle length of cyclic instability or may be variable length according to the implementation (e.g. half the length of the template used for correlation index).

Delta (DI): This index determines the extent or depth of instability in a patient signal and is calculated as:

$$DI(i) = f(i) - f(i-K) \quad \text{(Eq. 2)}$$

where f(i) is the current value of the feature used for analysis, and K is factor that is related to the cycle length of cyclic instability or may be a variable length according to the implementation (e.g., half the length of the template used for correlation index).

Event or Breath or Respiratory cycle Frequency (EFI): This index determines the periodicity of events, breaths, respiratory or other cycles, and is calculated as the frequency of cyclic changes.

Event or Respiratory cycle Harmonics (EHI): This index determines the periodicity of events, breaths, respiratory or other cycles, and is calculated as the harmonic frequency and power in the cyclic changes.

Event or Respiratory cycle Phase (EPI): This index determines the phase changes in the cyclic variations of events, breaths, respiratory or other cycle and is calculated as the phase of cyclic changes.

Flow Limitation Index: This index determines the existence of flow limitation in patient flow. Based on this index, if flow limitation is present, for example, the present invention contemplates increasing the PAP therapy pressure before $CO_2$ rebreathing or other therapy combination is delivered.

C. Classification and Prediction of Indices and Therapy Index Calculation

Figure 6:
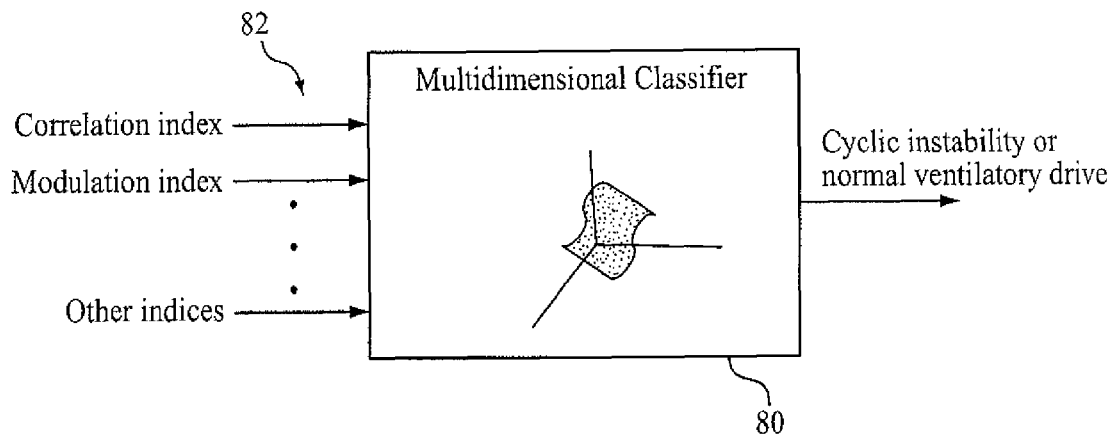
FIG. 6 is a graphical representation of a multidimensional classifier for computed indices.

Therapy index module 64 calculates the therapy index from the computed indices by using multiple implementations that include a multidimensional classifier and/or predictive models. In one exemplary implementation, therapy index module 64 uses a multidimensional classifier 80, as shown for example in FIG. 6, for multiple indices 82 computed for the ventilatory drive instability and flow limitation. Based on the time-scale used in the implementation (e.g. second-by-second or breath-by-breath), classifier 80 uses multiple indices to classify the time instance as ventilatory instability or normal ventilatory drive.

In another implementation, the derived indices are used with a linear or nonlinear predictive model to predict the future value of the indices. In a different implementation, probabilistic models based on Hidden Markov model (HMM) are implemented to predict the future value of the indices.

Figure 7:
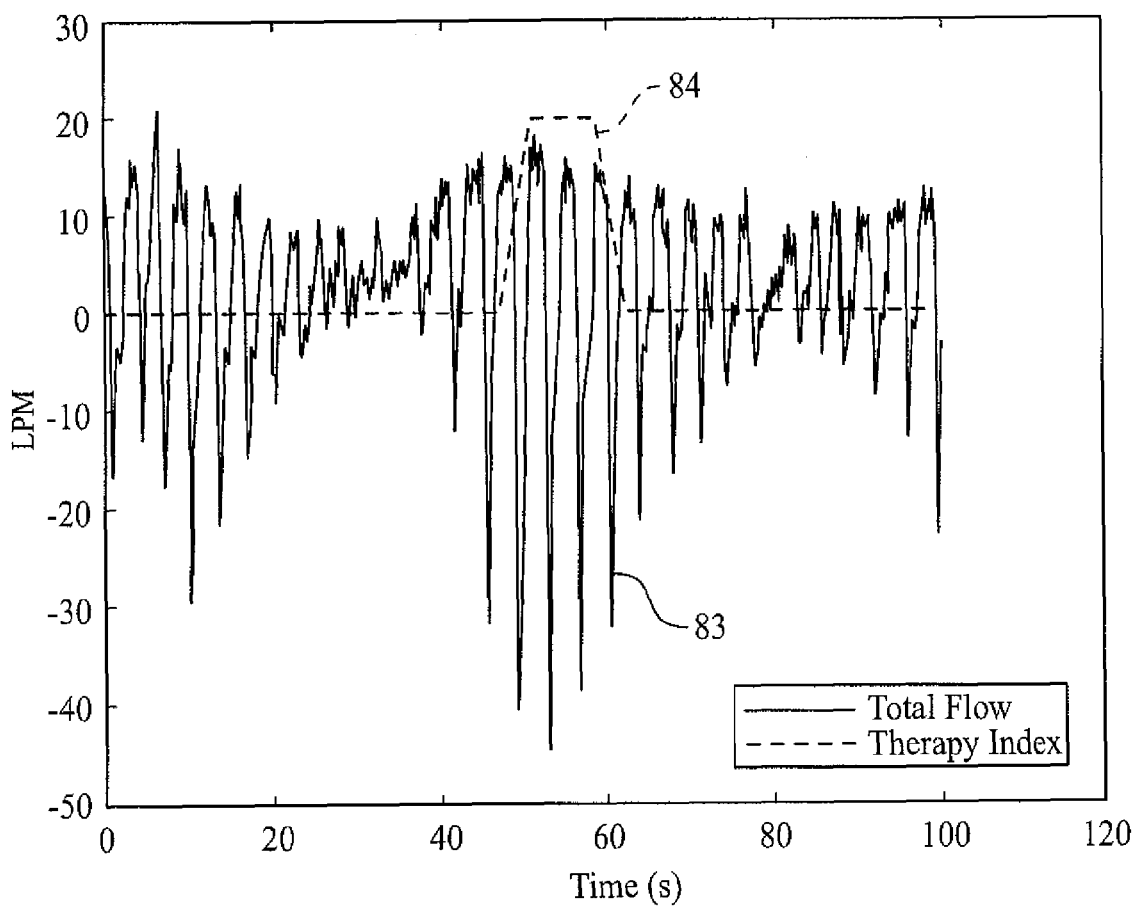
FIG. 7 is a graph of a flow waveform for one exemplary implementation of the detector algorithm according to the principles of the present invention using the patient flow signal.

An example of one of the implementations of therapy index module 64 in detector module 44 is shown in FIG. 7. In this example, the detector module extracts features and calculates indices from a patient flow signal 83 for each breath. An example of a feature that can be used is the difference between the maximum and the minimum patient flow during each breath. Based on this feature, therapy index module 64 calculates the modulation index and correlation index with a thirteen points long "V" shape template. Using a two-dimensional classifier to detect cyclic instability, a therapy index 84 is calculated that indicates the time and level of therapy for the controller module (shown in FIG. 7).

IV. Therapy Control Module

Controller module 46 controls the activation and deactivation of the therapy module to stabilize the cyclic respiratory instability. For each patient event, the algorithm in controller module 46 controls the time and duration of therapy intervention based on the therapy index that provides information about the extent of instability and cycling in patient's ventilatory control. As noted above, a block diagram for the controller algorithm is shown in FIG. 8 and the flow diagram is shown in FIG. 9.

A. Control of Therapy Type

In one or more implementations, controller module 46 determines the therapy intervention in block 70 used to treat the patient, which includes, but is not limited to, the following therapy treatment modes.

1. PAP Control for $CO_2$ Rebreathing Therapy

In one exemplary embodiment, the algorithm implements a PAP pressure control that allows the therapy device provide an auto-titration algorithm for PAP pressure control to include the effect of a $CO_2$ breathing therapy. That is, a PAP therapy can be delivered to the patient in a manner such that not all of the patient's exhaled $CO_2$ is washed out of the pressure support system, but some of the $CO_2$ is rebreathed by the patient. The use of an auto-titration CPAP device allows the PAP device to increase or decrease the level of positive airway pressure delivered to the patient. U.S. Pat. No. 6,932,084 describes an example of an auto-titration CPAP device.

For subjects with central apnea and ventilatory instability, central apneic events lead to the narrowing of upper airway may also lead to the closure of upper airway. In the absence of $CO_2$ breathing therapy, the auto-titrating device may administer a higher level of CPAP pressure to treat apnea/hypopnea in the patient.

The present invention contemplates providing an auto-titration therapy that includes the auto-titration of $CO_2$ breathing therapy and PAP pressure. An effective $CO_2$ breathing therapy for central sleep apnea will allow the therapy device to use a lower CPAP pressure to overcome flow limitation in the patient. The modified auto-titration algorithm increases and decreases levels of $CO_2$ rebreathing/breathing therapy and PAP pressure to achieve an effective therapy.

In another exemplary embodiment, the algorithm implements a PAP pressure control that allows the therapy device to decrease the PAP pressure during expiration to facilitate $CO_2$ rebreathing. In addition to closing the exhalation ports, for each breath the therapy algorithm can implement a decrease in PAP pressure during expiration to facilitate the flow of exhaled gas towards the blower.

In a still further exemplary embodiment, controller module 46 implements a PAP pressure control that allows the ventilatory therapy delivered to the patient by therapy module 58 to incorporate features such as those associated with the C-Flex™ or Bi-Flex® devices manufactured and distributed by Respironics, Inc. These devices deliver a proportional positive airway pressure (PPAP) therapy to the patient in which the pressure of the gas flow provided to the patient is set based on the flow generated by the patient. U.S. Pat. Nos. 5,535,738; 5,794,615; 6,105,575; 6,609,517; and 6,932,084, (collectively referred to as "the PPAP patents") the contents of which are incorporated herein by reference, teach a pressure support device capable of operating in a PPAP mode. Examples a device that adjusts the pressure delivered to the patient based on the patient's respiratory flow is the REMstar® Pro, Plus, or Auto with C-Flex™ or Bi-Flex® devices manufactured and distributed by Respironics, Inc. The term "C-Flex" refers to a device that provides a CPAP respiratory treatment therapy in which the pressure delivered to the patient is reduced in proportion to flow during expiration. The term "Bi-Flex" refers to a device that provides a bi-level respiratory treatment therapy in which either the IPAP or EPAP pressures are further reduced in proportion to flow.

In another embodiment, control module 46 implements a PAP pressure control that allows the therapy device to provide a bi-level positive pressure therapy to the patient. In this treatment therapy, the pressure of fluid delivered to the patient's airway varies or is synchronized with the patient's breathing cycle to maximize the therapeutic effect and comfort to the patient. During inspiration, the patient receives an inspiratory positive airway pressure (IPAP), and during expiration, the patient receives an expiratory positive airway pressure (EPAP) that is lower than the IPAP. An example of a pressure support device that provides "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa. U.S. Pat. Nos. 5,148,802; 5,313,937; 5,433,193; 5,632,269; 5,803,065; 6,029,664; 6,360,741; 6,626,175; 6,823,866; 6,920,875; 6,948,497; 7,000,612; 7,011,091; and 7,100,607, (collectively referred to as "the bi-level patents") the contents of which are incorporated herein by reference, teach a pressure support device capable of operating in a bi-level mode.

Providing a pressure therapy in a PPAP, bi-level, or a combination of these modes, allows the therapy device to deliver a PAP therapy with comfort and facilitates $CO_2$ rebreathing therapy. The present invention also contemplates implementing the activation of the PPAP and/or bi-level feature(s) during certain phases of the cyclic instability for increased comfort (e.g. decrescendo phase of CSR).

In another exemplary embodiment, control module 46 implements PAP pressure control that allows the therapy device to deliver brief pulses of increased positive pressure to stabilize the ventilatory control system. Pulses refer to an increase in PAP pressure for a duration shorter than the breath inspiratory time. The control module controls the time of activation of this mode in certain phases of respiratory cycles.

The therapy applied to the patient is such that this intervention causes a change in the patient's ventilatory control feedback that restores the ventilatory control to a stable state. This is in contrast to the treatments described in the '624 patent and the '132 patent, where the therapy is delivered to achieve a target ventilation to treat central sleep apnea.

2. Additional Gas Modulation Therapy Combined with $CO_2$ Rebreathing

In one or more implementation, the $CO_2$ rebreathing therapy can be combined with other gas modulation therapies, such as $CO_2$ and $O_2$ gas mixture breathing. This combination therapy control is similar to the $CO_2$ rebreathing control that implements therapy intervention that incorporates the information of respiratory cycle timing and ventilatory system dynamics. In one implementation, $O_2$ gas can be added to the breathing circuit when severe oxygen desaturation (i.e., a drop below the normal levels in the patient) is detected during the hyperpnea-apnea cycles. This allows the controller module to stabilize the ventilatory control system in an effective manner when there is an increased sensitivity to $CO_2$ changes in the presence of oxygen desaturations. This approach also allows the therapy system to conserve $O_2$ gas consumption.

3. Variable Deadspace Therapy Control

Controller module 46 also implements a gas modulation therapy that controls a variable deadspace by controlling a bank of exhalation ports located on the patient tubing that is attached to the therapy device. The level of therapy is determined by the distance of the exhalation port from the patient. That is depending on which ports are closed or open, the amount of $CO_2$ rebreathing through a different deadspace volume is controlled.

B. Control Schemes

Controller module 46, in block 72, controls the therapy delivered to the patient by controlling the time and duration of therapy activation with reference to the respiratory cycle, breaths, or events. This therapy intervention is based on the therapy index that provides the controller module with the information about the level of the ventilatory instability, the periodicity or cycle time of the instability, the instance of current breath, event, or cycle with respect the cyclic behavior.

Controller module 46 implements a control algorithm that increases or decreases the level of therapy by (1) the time of activation and (2) duration of activation. By controlling the time of therapy activation in the cyclic or periodic or quasi-periodic nature of the ventilatory control instability, the effect of the therapy can be controlled. The human ventilatory control system is a negative feedback system with feedback delay that relates to the response time of chemoreceptors. The cycle time of respiratory instability is related to the fast responding peripheral chemoreceptors and gives an estimate of delay in the feedback loop of the ventilatory control system. If the oxygen desaturation signal is monitored by the therapy device, then it provides information of increased sensitivity of peripheral chemoreceptors. The algorithm of the present invention activates the therapy based on the estimate of delay of peripheral chemoreceptor response and aligns the intervention with respect to the reference point of the cyclic changes in ventilation.

The controller module implements the following control schemes in one or more implementations of the therapy system of the present invention:

1. Binary (On/Off) Control

In this control algorithm, the therapy index is compared to a fixed preset threshold to classify the current respiratory cycle, breath, or an event as a cyclic instability event. If an instability event is classified, then a therapy 88 is activated for a fixed time and duration in the cycle or for fixed breath duration activated for a set number of breaths.

Figure 10A:
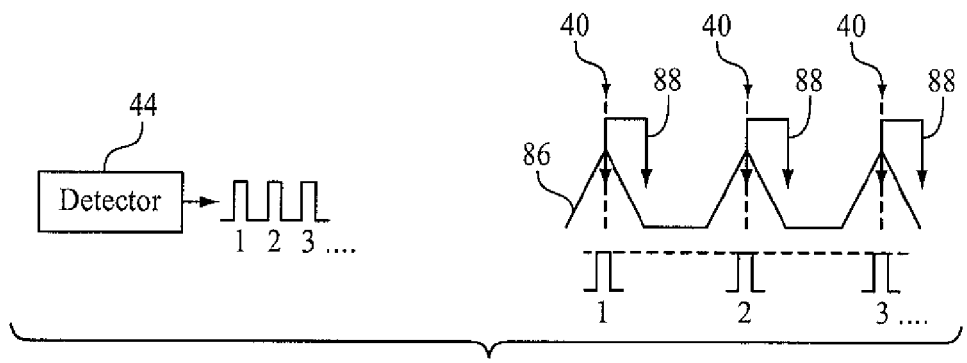
FIG. 10A-10D are charts illustrating the binary control and proportional control for therapy according to the principles of the present invention.
Figure 10B:
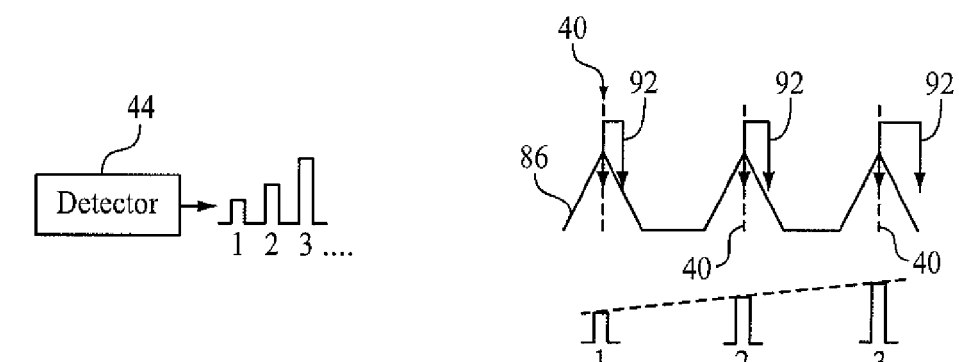
Figure 10C:
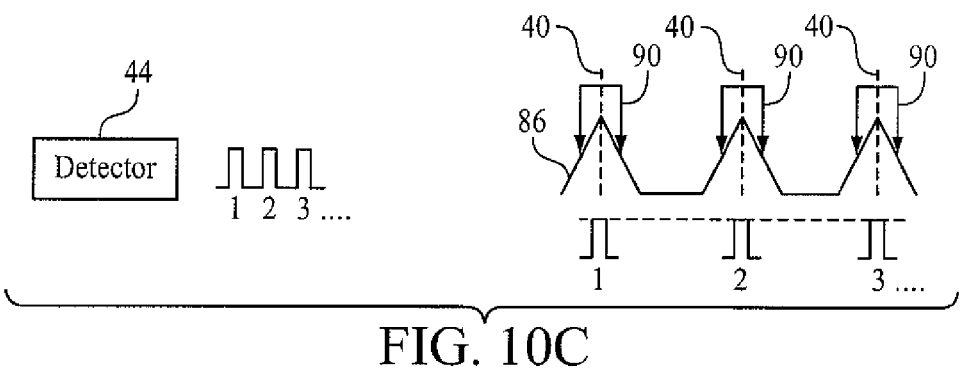

An example of the binary control is shown in FIGS. 10A and 10C. In this embodiment, a cyclic pattern of ventilatory instability is illustrated as waveform 86, with the peaks being detected and identified as reference point 40. In FIG. 10A, the therapy intervention 88 begins at reference point 40 and continues for a fixed duration for each instability pattern. In FIG. 10C, a therapy intervention 90 is centered about reference point 40. The duration for each therapy intervention 90 is fixed for each instability pattern.

2. Proportional Control

In this implementation, the time and duration of therapy is proportional to the level of therapy index. In one embodiment of the present invention, the therapy is activated closer to the cycle reference point and for a longer duration if the level of instability is high. In another implementation, the therapy can be activated earlier in the cycle and for a longer duration if the instability is higher and the level of oxygen desaturation is not severe. In yet another implementation, therapy can be activated for every other breath for lower levels of instability. The present invention also contemplates that the therapy duration can be controlled during the breath.

Figure 10D:
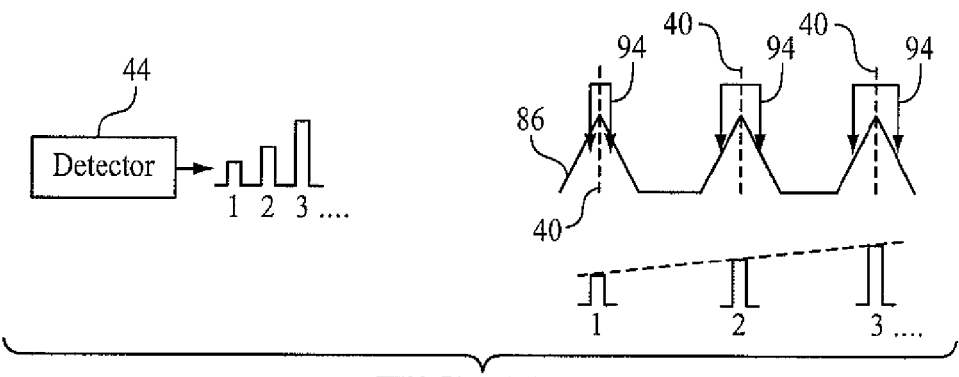

An example of the proportional control is shown in FIGS. 10B and 10D. In this embodiment, a cyclic pattern of ventilatory instability is illustrated as waveform 86, with the peaks being detected and identified as reference point 40. In FIG. 10B, a therapy intervention 92 begins at reference point 40 and continues for a duration that varies depending on, for example, the degree of instability, for each instability pattern. In FIG. 10D, a therapy intervention 94 is centered about reference point 40. The duration for each therapy intervention 94 is varied for each instability pattern based on the output of detector module 44.

3. Adaptive Control

Figure 11:
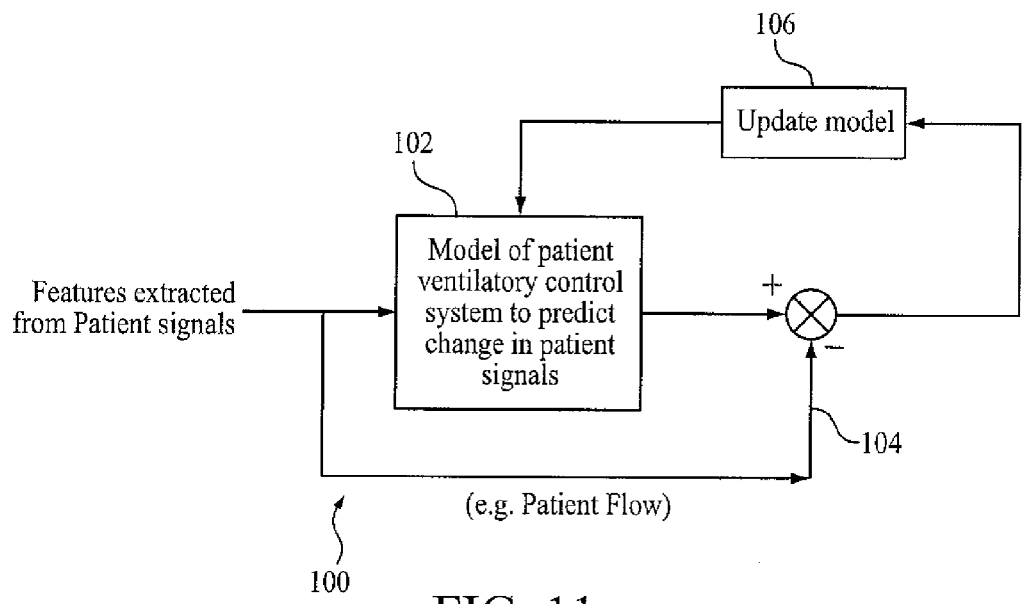
FIG. 11 is a block diagram illustrating the adaptive control scheme for therapy according to the principles of the present invention.

FIG. 11 illustrates an example of an adaptive control scheme 100 implemented by controller module 46. In adaptive control scheme 92, controller module 46 uses a simple model 102 of the underlying ventilatory system. The expected output 104 of system model 102 is compared to the actual effect 104 of the therapy intervention. For example, patient flow can be used as the patient signals. The model parameters are updated in block 106 based on this difference of the response and used to redefine the model 102.

4. Heuristics/Rule-Based Control

In this control scheme, the therapy activation is under rule-based control. The controller module uses heuristics or rule-based logic based on multiple indices.

5. Memory Based (Learning) Intelligent Control

In this control scheme, the controller module has the capability to learn from past effect of therapy activation and update the therapy control scheme to achieve stability in the ventilatory control scheme.

C. Control of Time and Duration of Therapy

Figure 12A:
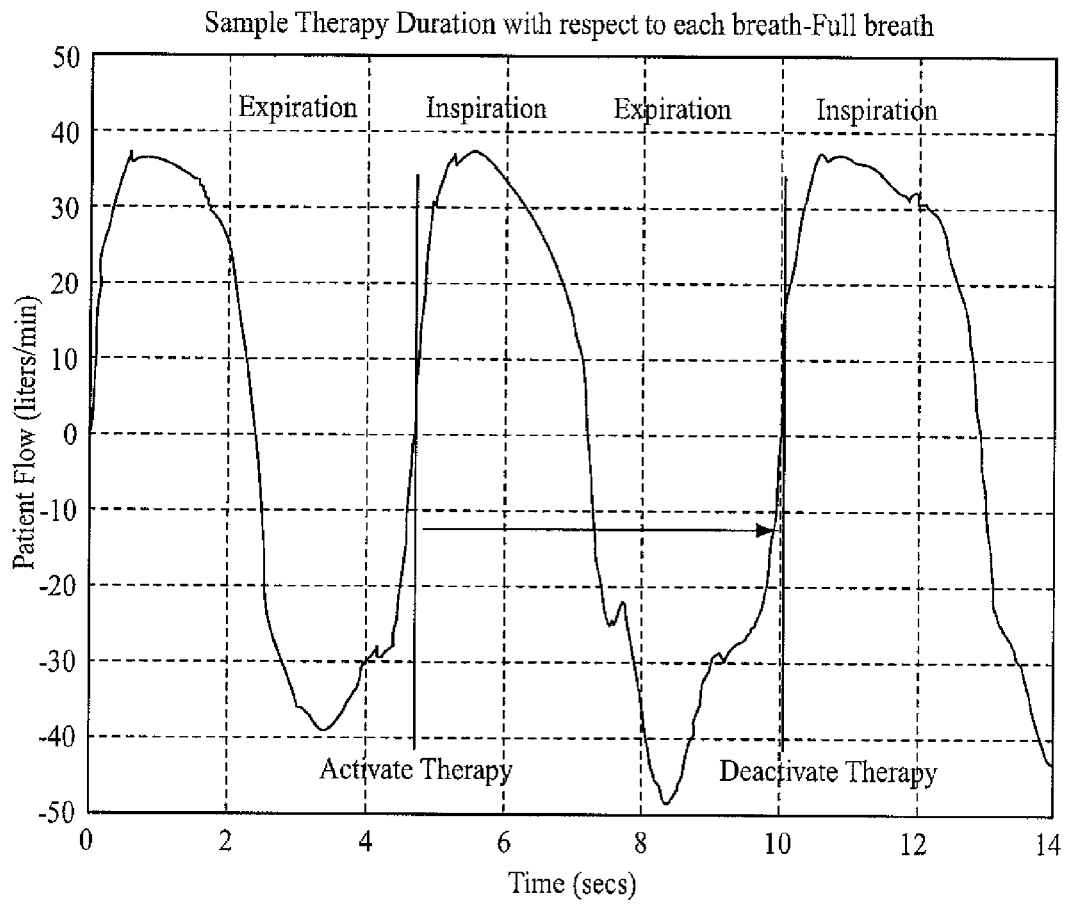
FIG. 12A is a chart illustrating the intra-breath control of therapy (full breath therapy duration according to the principles of the present invention.
Figure 12B:
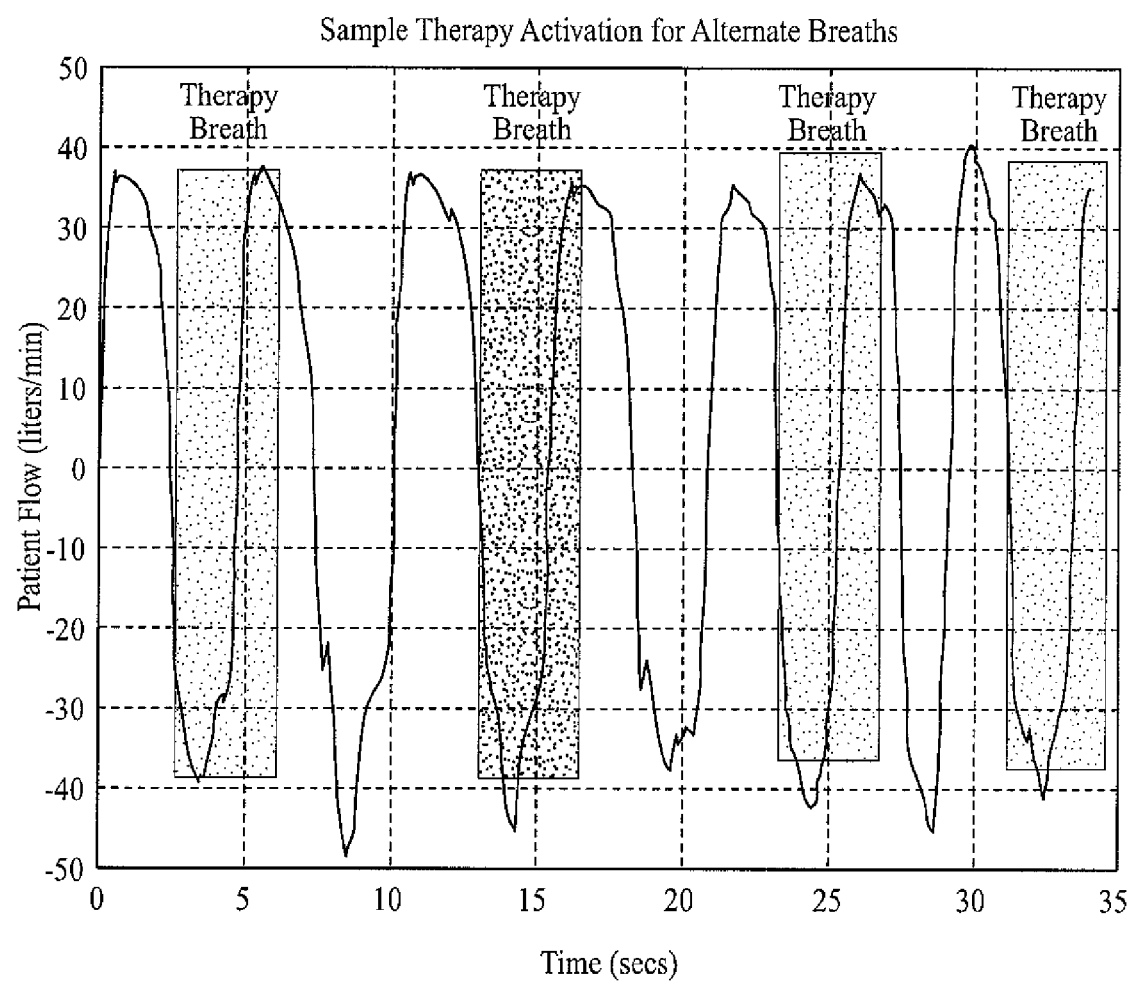
FIG. 12B is a chart illustrating an alternate breath control of therapy according to the principles of the present invention.

Controller module 46 implements the therapy intervention with multiple time-scales to achieve an effective therapy. The therapy intervention can be applied for events for one or multiple seconds, breaths, or respiratory cycles. FIG. 12A is a chart illustrating an intra-breath control of the therapy. In this embodiment, a full breath therapy duration is provided. FIG. 12B illustrates an alternate breath control of therapy in which the intervention is provided only during half of the breath, such as the expiratory phase. The present invention contemplates that controller module also implements time or delay control for early or late intervention during each of the following multiple time-scale events:

a) activation of therapy over multiple breaths or events with respect to respiratory cycle or event reference point,
b) intra-breath, intra-cycle, or intra-event duration of therapy (partial or full duration, or early/late inspiration or respiratory cycle or event), and
c) therapy activation for contiguous or alternate breaths, respiratory cycles, or events, or specifically selected breaths or events.

V. Actuator

Based on the therapy activation, actuator module 48 generates trigger signals 56, 56' for controlling the hardware and/or various components of therapy module 58 to provide the different therapy options. Actuator signals 56 are used to control various types of valves, actuators, diaphragms, servo-controls, etc, and may include one or more signals. Examples of actuator signals 56 include, but are not limited to binary (on/off) signal, sawtooth signal, pulse width modulated waveform (PWM), frequency modulated or frequency shift keying signal.

VI. Therapy Module

As noted above, the present invention contemplates that therapy module 28 is any device for treating the ventilatory instability. This can include a ventilatory therapy (which can include servo ventilation or other pressure support and can be done with or without $CO_2$ rebreathing induced by the ventilatory therapy), a gas modulation therapy, or both. FIGS. 13A-13F schematically illustrate six variations of a therapy system 110 that treats ventilatory instability by controlling $CO_2$ rebreathing. The therapy module shown in these figures includes a patient interface device 112, such as a nasal, oral, nasal/oral combination, or full face mask, a patient circuit 114, and a PAP system 116. In these embodiments, the hardware necessary to implement controlled rebreathing of $CO_2$ is an add-on option for the PAP system. Without the option, the PAP system is a standard PAP therapy device, such as a conventional CPAP system.

Figure 13A:
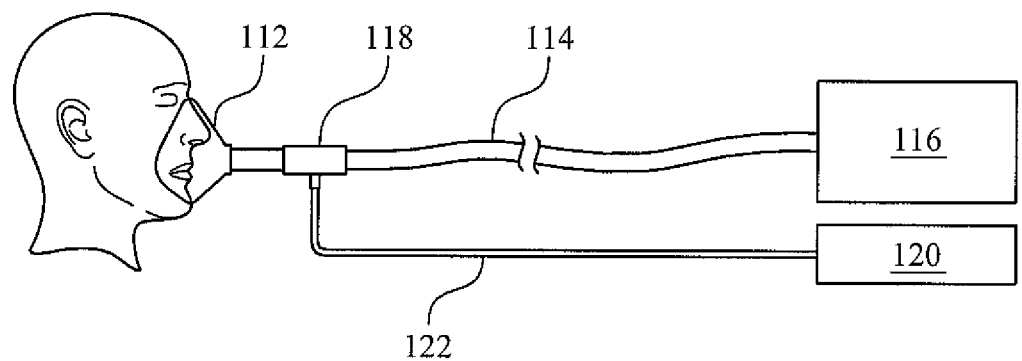
FIGS. 13A-13F schematically illustrate various embodiments a therapy system according to the principles of the present invention.

The therapy system of FIG. 13A includes a variable gas control valve with exhalation port 118 and a secondary pressure device and/or control system 120. A communication link 122 is provided between valve 118 and control system 120. The present invention contemplates that control system-variable gas control valve communication link 122 is a pneumatic or an electric, depending on the control requirements of a valve 118. Communication link 122 can also be integrated into, or connected adjacent to patient circuit 114.

In this embodiment, secondary pressure device and/or control system 120 is provided in a separate housing from PAP system 116. The functions of 42 can be provided in control system 120, PAP system 116, or both. Of course hardwired or wireless communication links will be needed between control system 120 and PAP system 116 to provide control and/or data signals between these components.

Figure 13B:
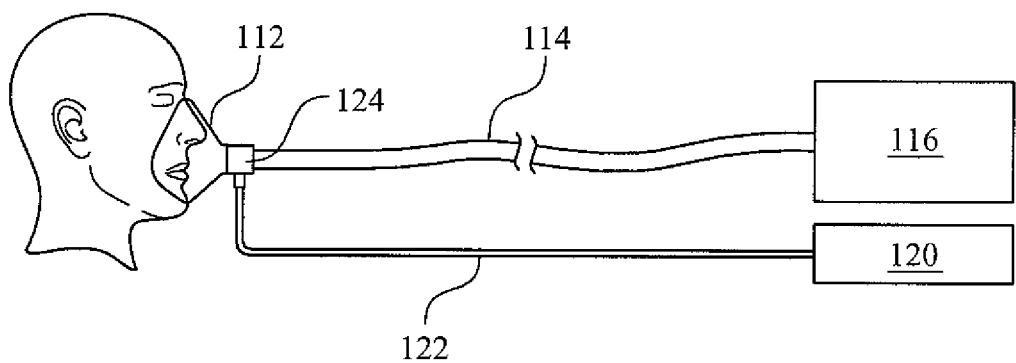

The therapy system of FIG. 13B is generally similar to that of FIG. 13A except that mask 112 includes a built-in valve and exhalation port 124 and valve 118 is eliminated. The present invention contemplates providing both valve 118 and valve 124 and controlling either or both to provide the desired level of rebreathing therapy.

Figure 13C:
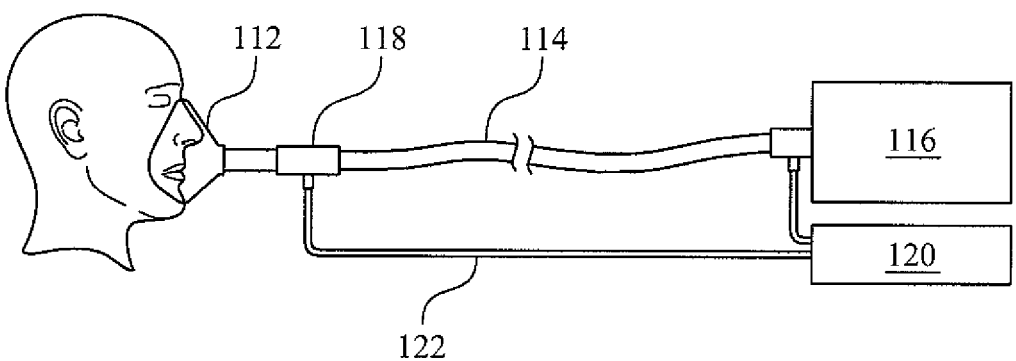
Figure 13D:
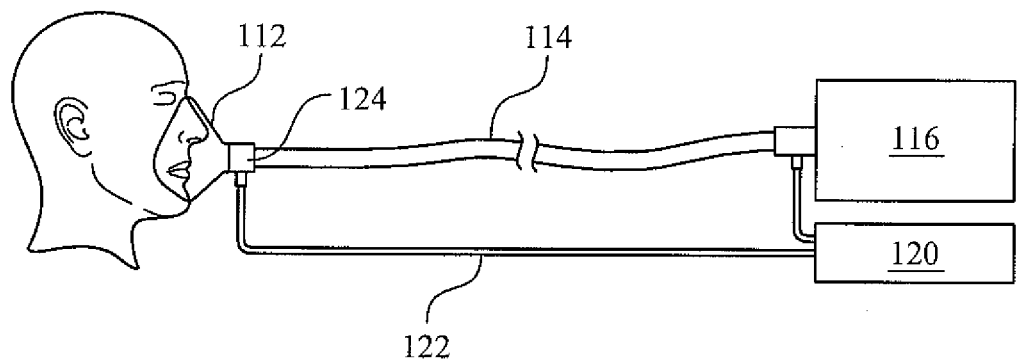

The therapy system of FIG. 13C is also generally similar to that of FIG. 13A, except that in this embodiment, PAP system 116 provides a secondary pressure signal 126 to control system 120. Alternatively, control system 120 could be embedded directly into the primary positive pressure device 116. The system of FIG. 13D is similar to that of FIG. 13C, except that it uses built-in valve and exhalation port 124 at mask 112.

Figure 13E:
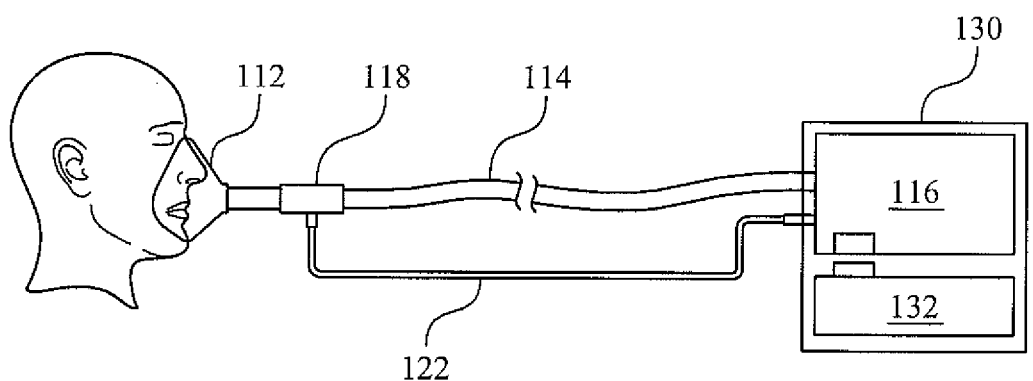
Figure 13F:
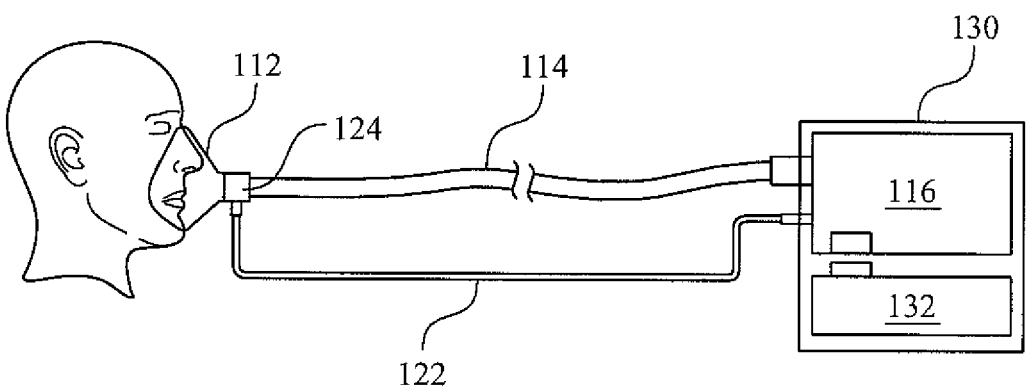

FIG. 13E illustrates a therapy system 110 in which PAP device 116 includes a controller docking port 130 to enable a valve control system module 132 to be coupled to PAP device 116. In an exemplary embodiment, the control system module 132 is docked to the bottom of PAP device 116. Of course, the present invention contemplates coupling or docking the valve control system to the pressure support system in any one of a variety of different configurations. The system of FIG. 13F is similar to that of FIG. 13E, except that it uses built-in valve and exhalation port 124 at mask 112.

It can be appreciated that the therapy system 110 in FIGS. 13A-13F provides an optional plug-in control module that connects to the PAP housing unit (either by being inserted into or connected with by wires, pneumatic circuits, or wirelessly means. Powering the control valve with pneumatic pressure can be accomplished using the output or intake of the PAP base unit blower, thereby eliminating the need for a separate pneumatic power source.

The present invention also contemplates that the control of valve 118 and/or 124 can be done electronically, assuming, of course, that valve 118, 124 is an electromechanical valve. In which case communication link 122 is a hardwired or wireless link between the valve and the valve controller. Of course, combinations of electronic, pneumatic, or mechanical connection are also contemplated by the present invention.

The present invention further contemplates that elements of the valve controller may be incorporated into the base PAP system. The net result of this is that there may only be a patient hose with an additional communications or valve control link that needs to be connected to the base unit, eliminating the need for a modular box enclosing a control circuit.

As noted above, there present invention contemplates other techniques for providing a treatment for the ventilatory instability. The following are alternatives techniques or various other ways of treating ventilatory instability using $CO_2$ rebreathing.

A. Varying the Distance of the Exhaust Port from the Patient Interface

It is known to provide an exhaust port in a patient circuit to exhaust gas, such as exhaled $CO_2$ from the otherwise closed system. It is further known to actively control this exhaust port to control the amount of gas vented to the ambient atmosphere, and conversely, the amount of $CO_2$ rebreathing by the patient. In these known systems, the location of the exhaust port is fixed on the patient circuit. This embodiment of the present invention, however, teaches a technique for varying the position of the exhalation vent port relative to the patient interface device. Changing the position of the exhaust port allows the amount of $CO_2$ rebreathing to be controlled.

Figure 14:
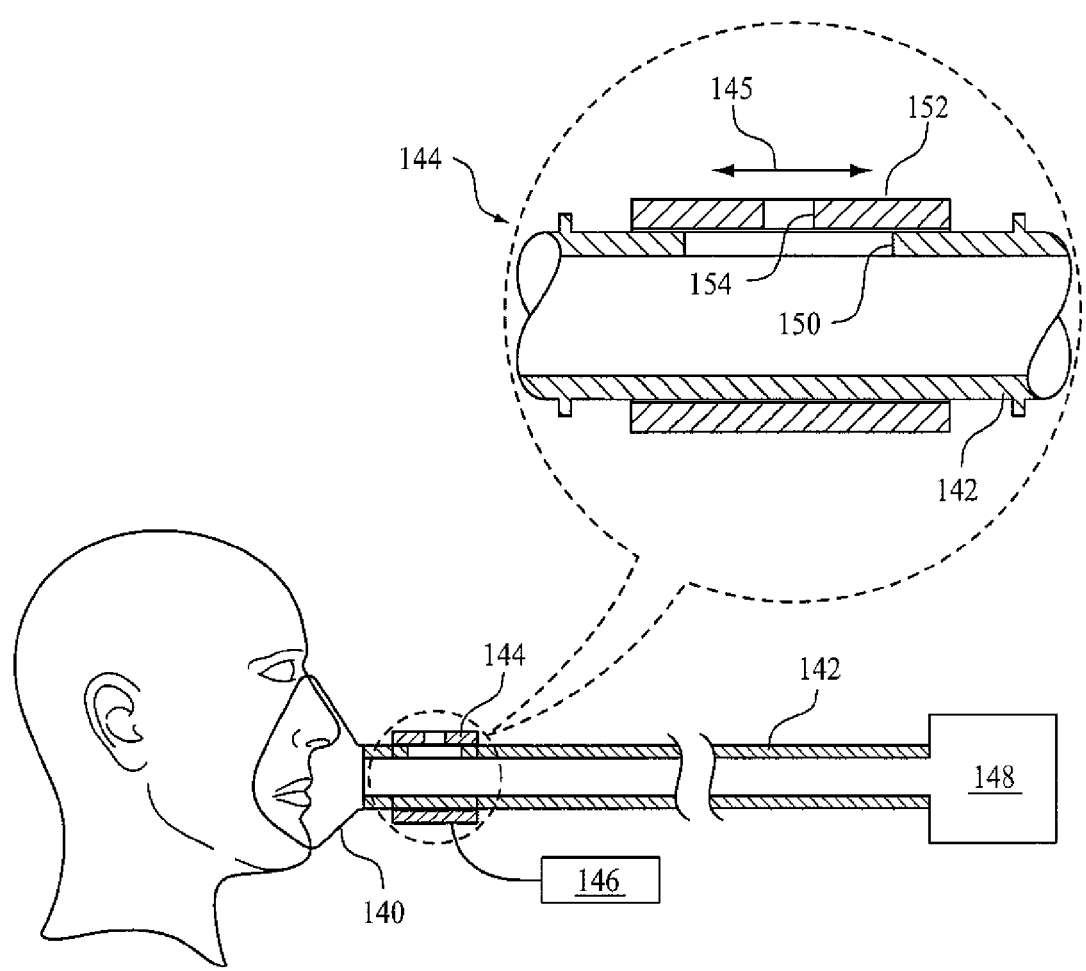
FIG. 14 is a cross-sectional view of a therapy system the includes a variable distance port.

As shown in FIG. 14, a mask 140, or other suitable patient interface device, is coupled to the patient's airway, and a patient circuit 142 is coupled to the mask. A mechanical and/or electrically controlled sliding valve 144 is provided in the path of the patient circuit. Valve 144 is moveable relative to the patient circuit, as indicated by arrow 145. Valve 144 is operated under the control of a valve controller 146, which can be either a stand alone device or incorporated into a PAP system 148, for example as an internal subsystem in the PAP system.

A relatively large (or long) vent or slot 150 is provided in patient circuit 142. A sleeve 152 of the valve 144 is disposed over at least a portion of the patient circuit where slot 150 is located. In the illustrated embodiment, sleeve 152 surrounds patient circuit 142. However, sleeve 152 need not fully surround the patient circuit. An opening 154 is provided in sleeve 152. Opening 154 is aligned with vent 150 to provide a gas flow path from the interior of the patient circuit to the ambient atmosphere. Moving sleeve 152 causes the location of opening 154 to move relative to the mask, thereby changing the amount of deadspace between the patient's airway and the exhaust path to the ambient atmosphere. The ability to change this deadspace allows the user to change the amount of $CO_2$ rebreathing by the patient.

It is to be understood that the present invention contemplates a variety of different configurations for valve 144, sleeve 152, vent 150, opening 154, and the manner in which the sleeve is moveable relative to the patient circuit. For example, vent 150 and opening 154 can have a variety of shapes and sizes. In addition, more than one vent 150 and/or opening 154 can be provided. Also, sleeve 152 can rotate in addition to or in place of slide relative to the patient circuit so as to align different opening with different vents in the patient circuit, thereby changing the effective distance of the exhaust path relative to the patient's airway.

Figure 15:
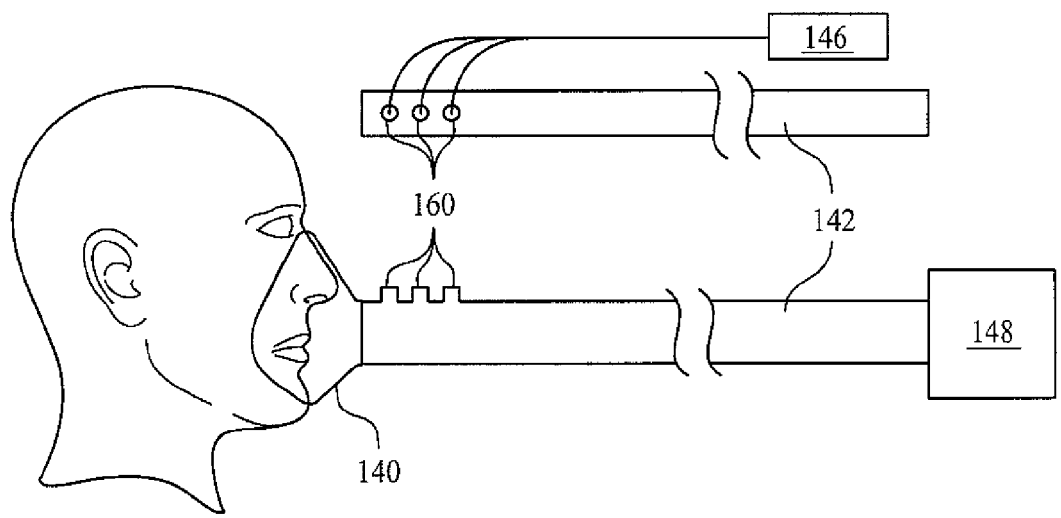
FIG. 15 is a side view of a therapy system that includes multiple exhaust ports.

FIG. 15 illustrates a therapy system that also alters the effective distance of the exhaust path relative to the patient airway. In this embodiment, a plurality of vent ports 160 are provided in patient circuit 152, which each vent port vent spaced a different distance from mask 140. In the illustrated exemplary embodiment, vent ports 160 have a common size and shape, and are spaced at even intervals along the patient circuit. The present invention contemplates, however, that any of these three characteristics, as well as any other characteristics, for the vent ports can be altered, alone or in combination with the others.

A valve mechanism is associated with each vent port to selectively block, either completely or partially, each vent port individually. Valve controller 146 controls the actuation of the valve mechanisms to select which vent ports are opened and which are closed. In the manner, the valve controller can vary in distance of the exhaust path from the patient circuit to the ambient atmosphere relative to the patient interface device. The present invention contemplates that the blocking or partial blocking of portion 160 can be controlled pneumatically, electrically, or by using electrically reactive material that would open and close respective vent ports.

B. Changing Deadspace by Changing the Volume of the System

Rather than change the physical location of the vent on the patient circuit to control the distance between the patient and the vent, thereby controlling the deadspace and $CO_2$ rebreathing, the present invention also contemplates changing the volume of the patient circuit or mask to control the amount of deadspace. For example, the present invention contemplates changing the physical length of the patient circuit between the patient and the vent to change the volume and resulting deadspace, adding volumes to the patient circuit, and/or changing the volume within the mask.

Figure 16:
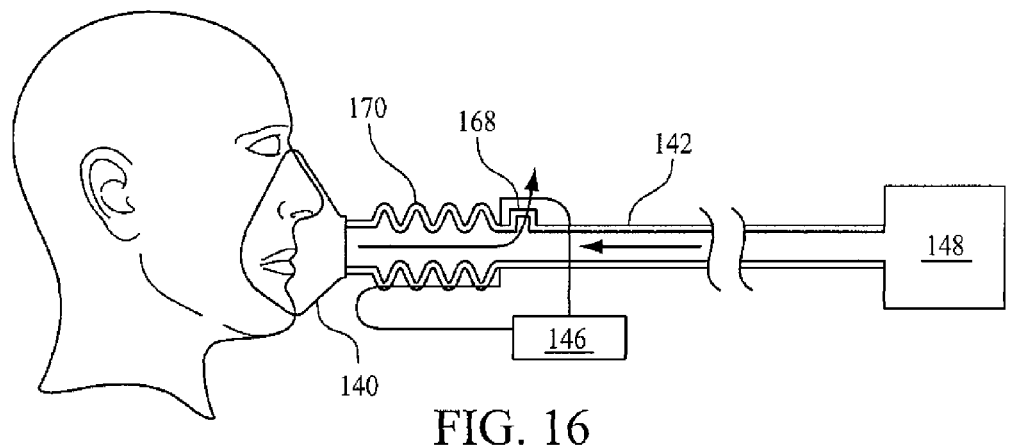
FIG. 16 is a sectional view of a therapy system that allows for automatic lengthening and shortening of the patient circuit.

FIG. 16 illustrates one example of a therapy system that accomplishes the function of controlling deadspace by changing the physical length of the patient circuit between the patient and the vent. In this embodiment, patient circuit 142 includes a variable length portion in the form of an expansion/contraction tube 170, which is provided between mask 140 and vent 168. The length of tube expansion/contraction 170 is changed via a control system 146 by means of a mechanical or electrical control using any conventional technique, such as a servo-motor that compresses the spring-like tube 170.

Figure 17:
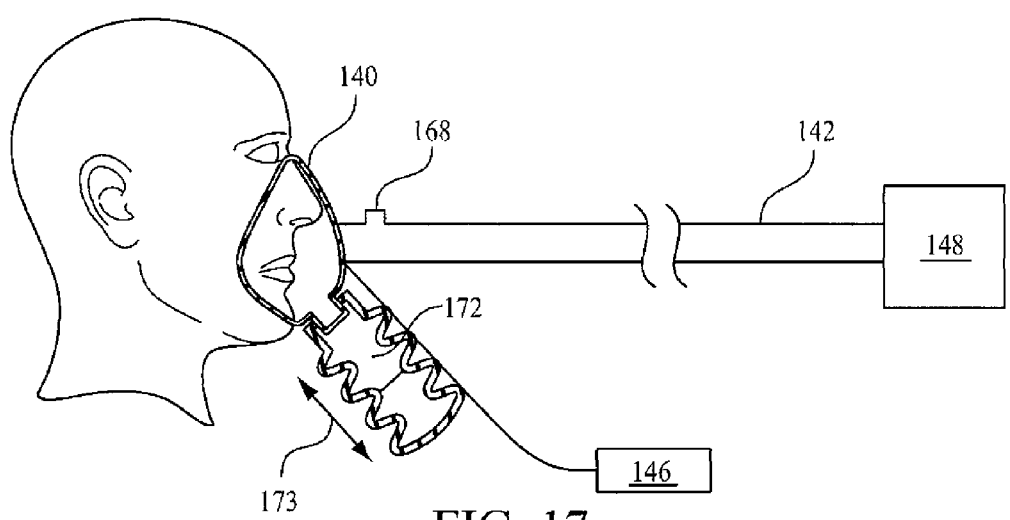
FIG. 17 is a side view of a therapy system with an adjustable volume on the patient interface device.

FIG. 17 illustrates an example of a therapy system that accomplishes the function of controlling deadspace by changing the overall volume of the patient circuit. In this embodiment, an adjustable reservoir 172 is coupled to mask 140. The overall volume of reservoir 172 is adjusted automatically as indicated by arrow 173 by therapy control system 146 using any conventional technique. It can also be appreciated that adjustable volume 172 can be added at other locations along the patient circuit, so long as it is provided between the patient's airway and exhaust vent 168.

Figure 18:
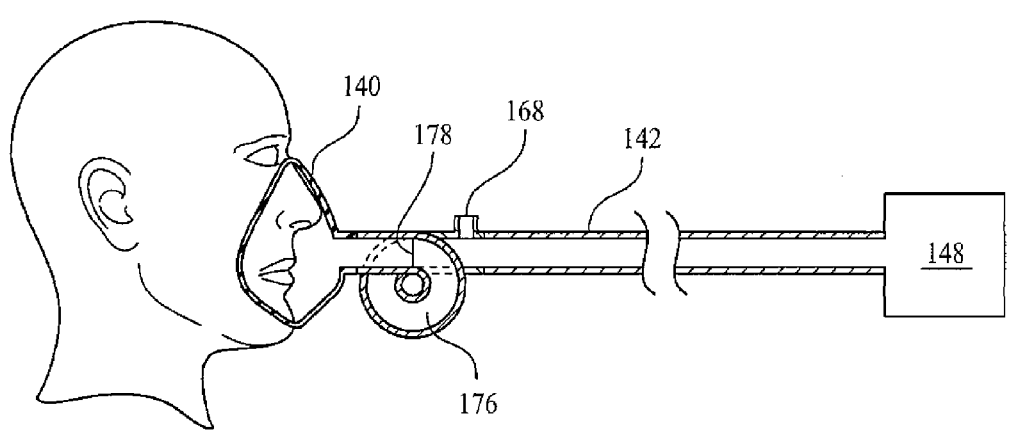
FIG. 18 is a sectional view of a therapy system that allows for additional volume to be added to the patient circuit.

FIG. 18 illustrates an example of a therapy system that accomplishes the function of controlling deadspace by selective adding a preset volume 176 or reservoir in-series with patient circuit 142. A valve 178 is provided to add volume 176 to the patient circuit or to cause the flow of gas to bypass this additional volume. Valve 178 is actuated by a valve controller (not shown) when the deadspace, i.e., $CO_2$ rebreathing, is to be added or removed. An example of a system that is capable of selectively adding a length of tubing to a patient circuit is taught by U.S. Pat. Nos. 6,042,550; 6,098,622; 6,227,196 and 6,408,848, the contents of which are incorporated herein by reference.

Figure 19:
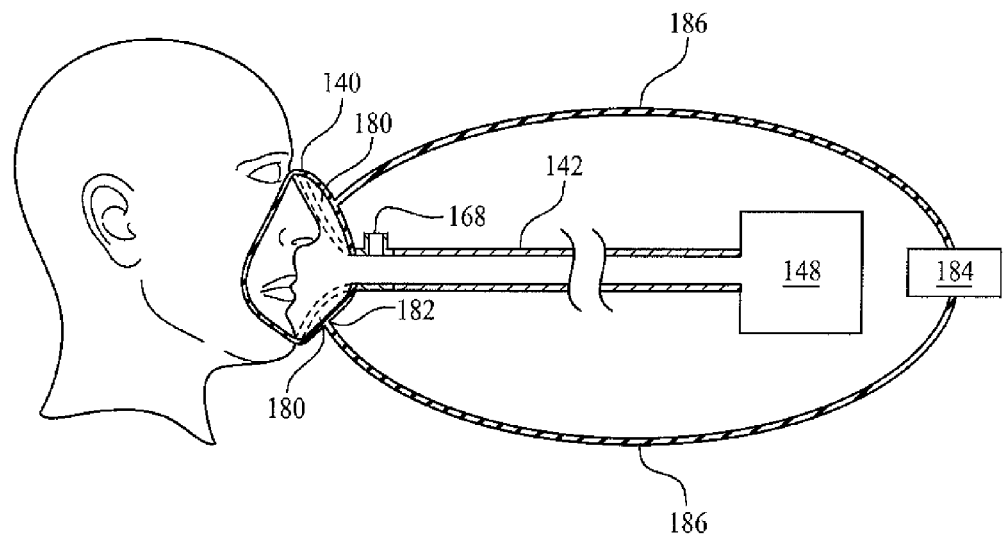
FIG. 19 is a sectional view of a therapy system includes a variable volume mask.

FIG. 19 illustrates an example of a therapy system that accomplishes the function of controlling deadspace by changing the volume within mask 140. In this embodiment, patient interface device, e.g., mask, 140 includes one or more sections 180 imbedded in the internal region of the mask. Sections 180 can be inflated and deflated to vary the amount of dead space within the mask, thereby providing whatever deadspace is needed in order to provide the gas modulation therapy to treat the ventilatory instability.

In order to function, sections 180 are connected to a source of gas for inflating or deflating these sections. To achieve this, interface device 140 includes inflation ports 182 that are connected to either a positive pressure device 148 or a standalone pressure source 184 by tubing 186.

C. Variable Size/Volume Patient Interface

Figure 20:
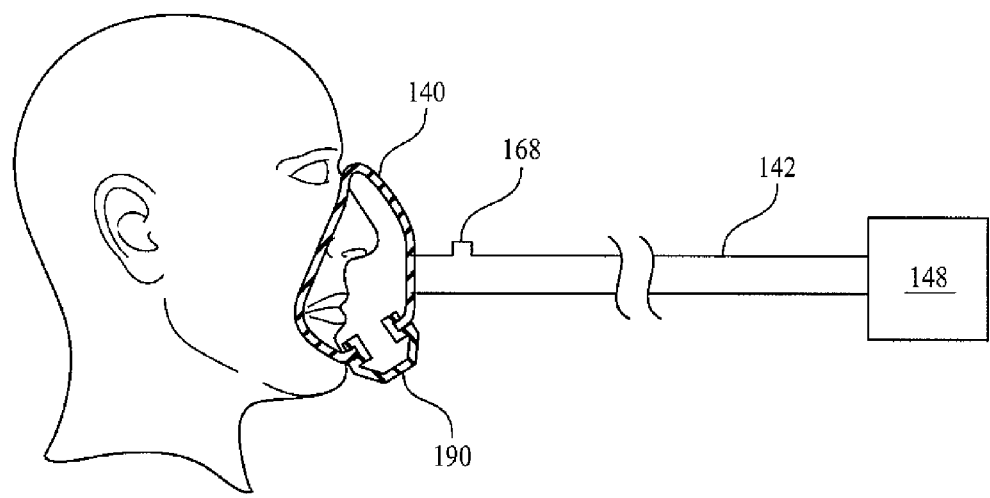
FIG. 20 illustrates a therapy system, partially in section, that includes a selectively volume mask and/or reservoir volume.

A more passive approach to controlling the amount of deadspace is shown in FIG. 20. In this embodiment, the amount of dead space is varied by selecting one of a series patient interface devices, e.g., masks having different preset volumes. In addition, or in the alternative, the user can select one of a plurality of reservoirs 190 having different volumes. The selected reservoir 190 is attachable to mask 140. Depending on the volume of the reservoir attached the mask, a different level of rebreathing will occur. Thus, in this embodiment, there are a set of available fixed-volume interfaces 140 and/or reservoirs 190 from which the clinician can choose. Because this approach is passive, it may not be well suited for dynamic alteration of the deadspace (hence $CO_2$ levels) on a breath-to-breath basis.

D. Patient Circuit that Captures $CO_2$

Figure 21A:
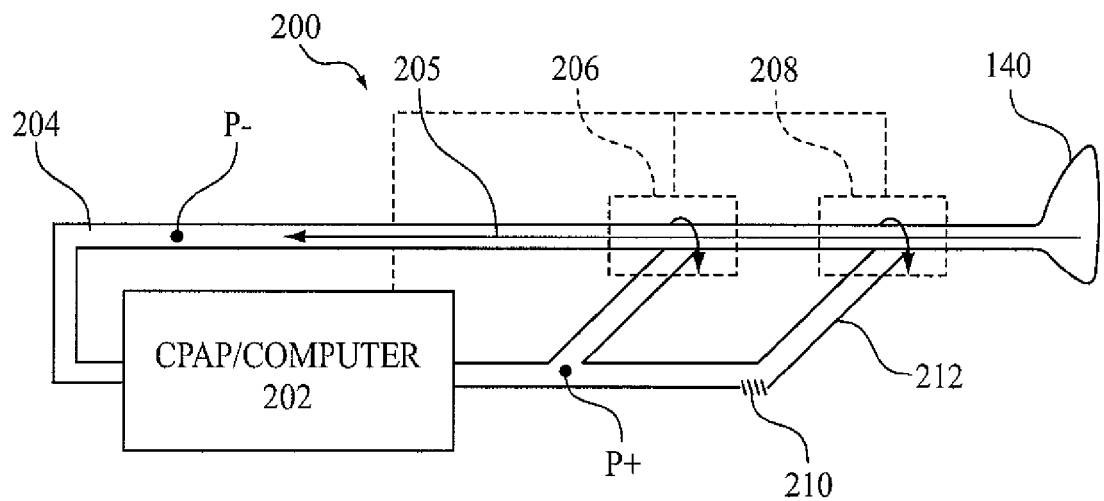
FIG. 21A-21C schematically illustrate a therapy system that includes a breathing circuit adapted to capture and redelivery exhaled $CO_2$.
Figure 21B:
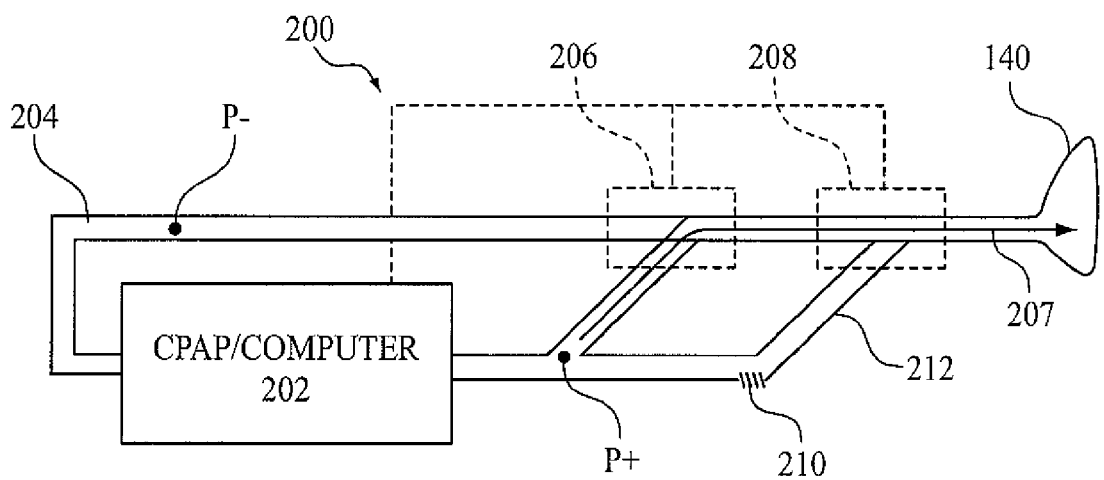
Figure 21C:
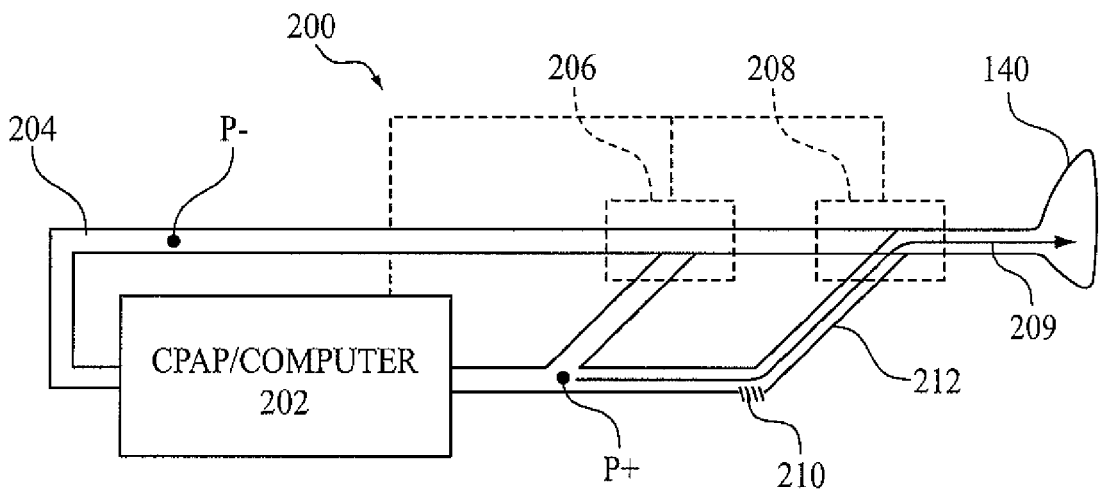

FIG. 21A-21C schematically illustrate a therapy system 200 that uses negative pressure (P−) to control the amount of $CO_2$ rebreathing experienced by the user. In this embodiment, negative pressure from the PAP system 202, such as a CPAP unit, is used to channel exhalation flow into a tubing 204 between a first valve 206 and a second valve 208. One end of tubing 204 is connected to the inlet of the blower in the PAP unit, which is at a negative pressure relative to the ambient atmosphere, and the other end is connected to mask 140. Valves 206 and 208 are controlled by a controller, which, in this embodiment, is shown being included in CPAP unit 202.

During exhalation, the $CO_2$ enriched exhaled gas flow retrograde into tubing 204, as indicated by arrow 205. During inhalation, valves 206 and 208 can be configured to provide two options: 1) valves 204 and 206 can be set so as to channel the $CO_2$ enriched mixture from tubing 204, i.e., the $CO_2$ enriched gas trapped between valves 206 and 208, to the patient, as shown in FIG. 21B and indicated by arrow 207, or 2) valves 204 and 206 can be set so as to channel clean air into the patient's inflow, as shown in FIG. 21C and indicated by arrow 209. An exhaust vent 210 is provided in limb 212.

E. Gas Modulation Therapy Including Supplemental Oxygen

Figure 22:
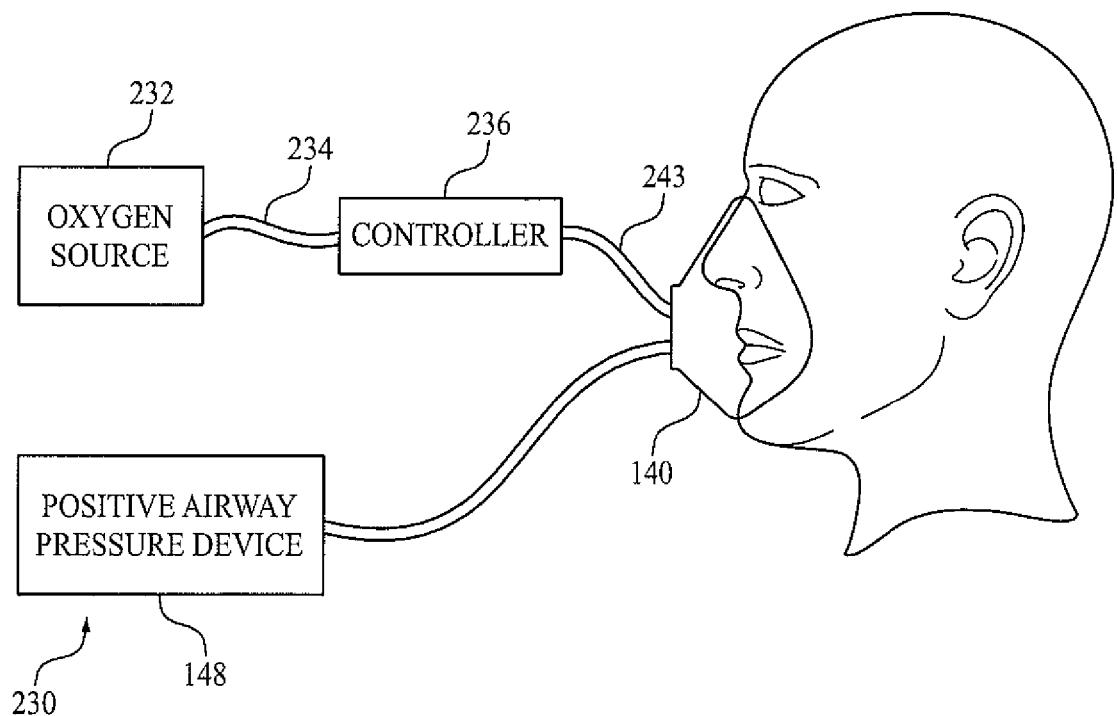
FIG. 22 schematically illustrates a therapy system that includes a combination of oxygen, servo-ventilation, and rebreathing exhaled $CO_2$.

As noted above, the present invention contemplates providing a treatment therapy to the patient that includes changing the fraction of inspired $O_2$ delivered to a patient using the therapy module. FIG. 22 illustrates a therapy system 230 that provides this type of gas modulation therapy, either alone or in combination with a ventilatory therapy or other gas modulation therapy. Therapy system 230 includes an oxygen source 232 and components 234, such a cannula or tubing, for delivering oxygen from the oxygen source to the patient. In the illustrated embodiment, therapy system 230 also includes an optional PAP system 148.

Oxygen source 232 can include, but is not limited to, an oxygen concentrator, a canister of gaseous oxygen, or a canister of liquid oxygen, or any other source of oxygen. In an exemplary embodiment, oxygen is delivered to the patient through tubing 243 that attaches from the oxygen source to mask 140 or at an alternate point in breathing circuit 142. A controller 236 controls when the oxygen is delivered and how much oxygen is delivered to the patient.

Oxygen can be delivered as described above to treat a ventilatory instability. The present invention also contemplates that oxygen can be delivered to the patient at a continuous or variable flow rate throughout the night. It can be triggered to be delivered only during inspiration. It can also be triggered to be delivered only during certain times of the sleep period, for example during periods of periodic breathing, or after hyperventilation is detected or after an arousal is detected.

The oxygen therapy can be discontinued when the patient's breathing is stable. In an exemplary embodiment, controller 236 is a processor and a proportional valve that operated under the control of the processor. The processor runs software that controls when the proportional valve is fully open, fully closed, or partially open as well as the degree to which the valve is open. The controller can receive inputs from sensors on the patient, including but not limited to nasal air flow, oxygen saturation, and mask pressure.

F. Separation of $CO_2$ from Exhaled Gas

Figure 23:
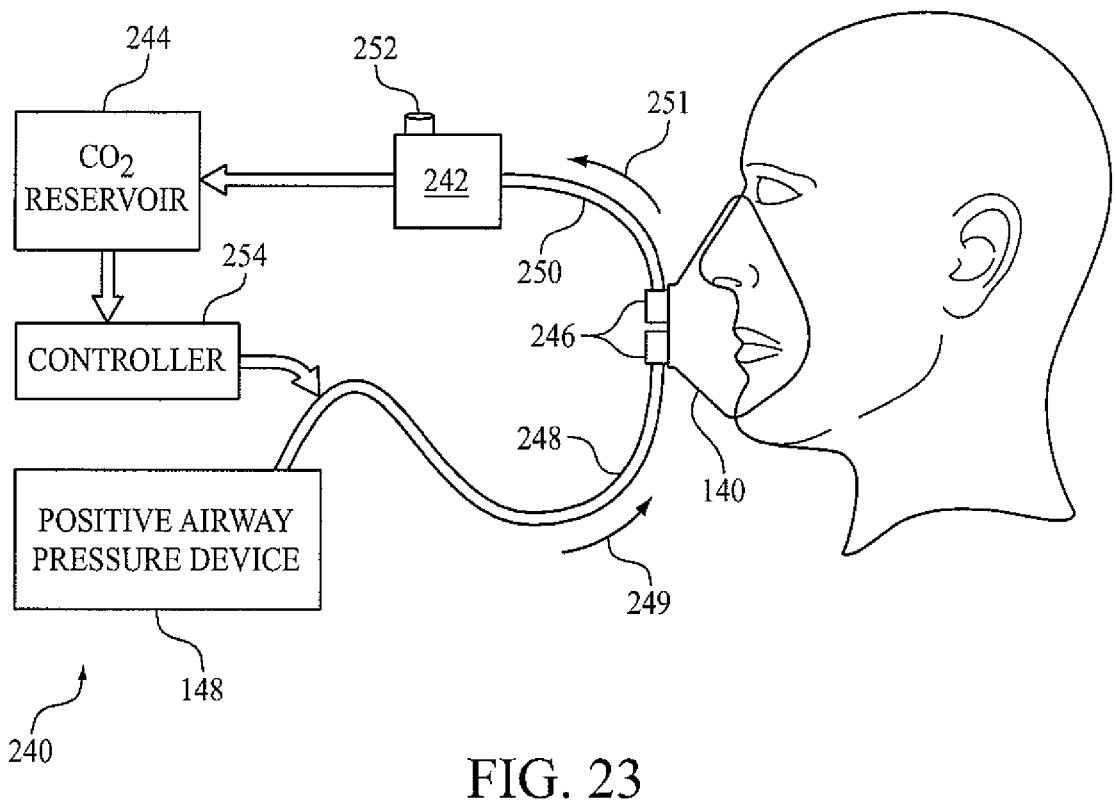
FIG. 23 schematically illustrates a therapy system that recaptures $CO_2$ from exhaled air and redelivery of $CO_2$ to the patient.

FIG. 23 illustrates a further embodiment of a therapy system 240 that uses a $CO_2$ scrubber 242 to separate carbon dioxide from the patient's exhaled air. $CO_2$ scrubber is any device that can remove $CO_2$ from the exhaled gas, such as a membrane that selectively allows $CO_2$ to cross the membrane, or a membrane that selectively allows oxygen and nitrogen to cross the membrane leaving the $CO_2$. Similarly, the oxygen and nitrogen can be chemically scrubbed from the exhaled air resulting in an increased concentration of $CO_2$. Once the $CO_2$ is separated it is stored in a reservoir 244 for subsequent delivery to the patient. One way valves 246 are provided to control the flow of gas so that the patient inspires through one set of tubing 248, as indicated by arrow 249, and exhales through the second set of tubing 250, as indicated by arrow 251. Due to operation of positive airway pressure 148 device, both sets of tubing have a positive pressure. In the expiration limb, this positive pressure forces the exhaled gas through the $CO_2$ removal device, which preferentially separates out $CO_2$ into reservoir 244. The remaining exhaled gas is exhausted through an exhaust port 252.

Once carbon dioxide is captured and stored, it is available to be delivered to the patient. The $CO_2$ can be delivered to the patient through a tubing that attaches from the $CO_2$ reservoir to the patient's mask or at an alternate point in the breathing circuit. A controller 254 controls when the $CO_2$ is delivered to the patient and the amount of $CO_2$ delivered.

In addition to the therapy treatment techniques noted above, $CO_2$ can be delivered to the patient at a continuous or variable flow rate throughout the night. It can be triggered to be delivered only during inspiration. It can also be triggered to be delivered only during certain times of the sleep period, for example during periods of periodic breathing, or after hyperventilation is detected or after an arousal is detected. The $CO_2$ therapy can be discontinued when the patient's breathing is stable. Additionally the amount of $CO_2$ delivered to the patient could vary. With higher amounts of $CO_2$ delivered when a leak is detected and lower amounts delivered when there is no or minimal leak.

The present invention contemplates that controller 254 includes a processor and a valve. The processor runs software that controls when the valve is open, closed, partially open, and to what degree. The controller can receive inputs from sensors on the patient, including, but not limited to, nasal air flow, total flow, end-tidal $CO_2$, transcutaneous $CO_2$, mask pressure and leak.

G. Optimizing $CO_2$ Delivery

The present invention further contemplate a technique for estimating the circulation delay in a patient's ventilatory feedback loop to control and optimize the treatment therapy, in particular, the $CO_2$ gas modulation therapy, whether provided through rebreathing or through the instruction to $CO_2$ to the patient from a $CO_2$ source. The instability in the human ventilatory control system is caused by increased circulatory delay and/or increased sensitivity of the chemoreceptors and/or increased gain of the plant. The prevent inventors recognized that a $CO_2$ gas modulation therapy can be optimized and better administered and controlled by estimating the circulatory delay in the ventilatory control system.

In an exemplary embodiment, the circulation delay is estimated by (i) monitoring respiratory cycling, such as CSR, in patient flow or tidal volume, (ii) monitoring cyclic changes in SpO2 that are attributed to the respiratory instability, (iii) monitoring cyclic variations in heart rate/R-R intervals and photoplethysmogram signals, or any combination of (i)-(iii). The cyclic changes in patient flow and tidal volume correlate with the circulation delay in the feedback control loop and each phase (crescendo, decrescendo, or apnea/hypopnea) approximately corresponds to the circulation delay from lung to carotid bodies. The delay between the first breathe after apnea and the nadir in SpO2 also similarly gives circulatory delay from lungs to carotid bodies with additional transport delay to the site of oximetry. The circulation delay can be predetermined during the diagnostic study or can be estimated during the therapy. During diagnostic study, interventions that can be used include breath holding followed by deep inspiratory breath.

In addition to estimating the circulatory delay, the oxygen desaturation (SpO2) signal can be also used to determine the level of $CO_2$ delivery. With severe oxygen desaturations, the $CO_2$ delivered to the patient is scaled back and/or initiated at the appropriate time to allow for normal oxygen levels during breaths after the apneic phase in the cycle. This parameter can also be used to determine if a combination therapy with oxygen, for example, is a more appropriate therapy for the patient.

A photoplethysmogram (PPG) sensor can be added to the $CO_2$ therapy system to control the therapy by identifying and differentiating between central and obstructive apneic events. The changes in intrathoracic pressure with inspiration and expiration are seen in a PPG signal as pulsus paradoxus. The PPG signal can be acquired by a transmittance or an infrared reflectance sensor. The PPG sensor can be attached to different body sites that include earlobe, nose/nares, mastoid, forehead, wrist, finger, or toe or can be mounted in the patient interface for contact at an appropriate facial site.

These respiration related variations in the PPG signal can be monitored by the amplitude and frequency changes in PPG signal. By monitoring the PPG signal power in the respiratory frequency, it can be determined if there is a central apnea or an obstructive apnea. This information can be used to control the $CO_2$ gas modulation therapy so that it is initiated only for central apneas and not for obstructive events. The respiration related parameters derived from the PPG signal also provide information about the work or effort of breathing that can be used for control of the $CO_2$ therapy algorithm.

The present invention further contemplated providing a $CO_2$ sensor in the therapy system and using the output of the sensor to control the $CO_2$ gas modulation therapy provided to the subject. For example, an end-tidal $CO_2$ sensor or a transcutaneous sensor can be used to monitor the change in $CO_2$ levels. These changes are useful in determining when to initiate and how to control the duration of the $CO_2$ therapy.

Additionally, the present invention contemplates monitoring the variability in physiologic parameters in order to identify sleep states (e.g., wake, NREM, REM) to further optimize the $CO_2$ therapy. The present inventors recognized that the hypocapnic $CO_2$ levels are different in NREM and REM sleep states, with $CO_2$ levels being more labile during NREM as compared to REM state. The identification of sleep states is useful in optimize the $CO_2$ gas modulation therapy for treating respiratory instability primarily seen in NREM sleep. The parameters that can be used to estimate the sleep state include respiration rate, PPG signal frequency, flow, and heart rate/R—R intervals.

H. Alternative $CO_2$ Gas Modulation Therapy

The present invention includes an apparatus that controls the flow rate out of the breathing circuit (allowing exhaled gas to be flushed out of the system). The apparatus can perform as a binary valve with 2 states (open or closed) or a proportional valve where multiple states are possible. The state of the apparatus changes using an electromechanical component, pneumatics, or a similar mechanism and is actively controlled by the patients breathing pattern.

Figure 24:
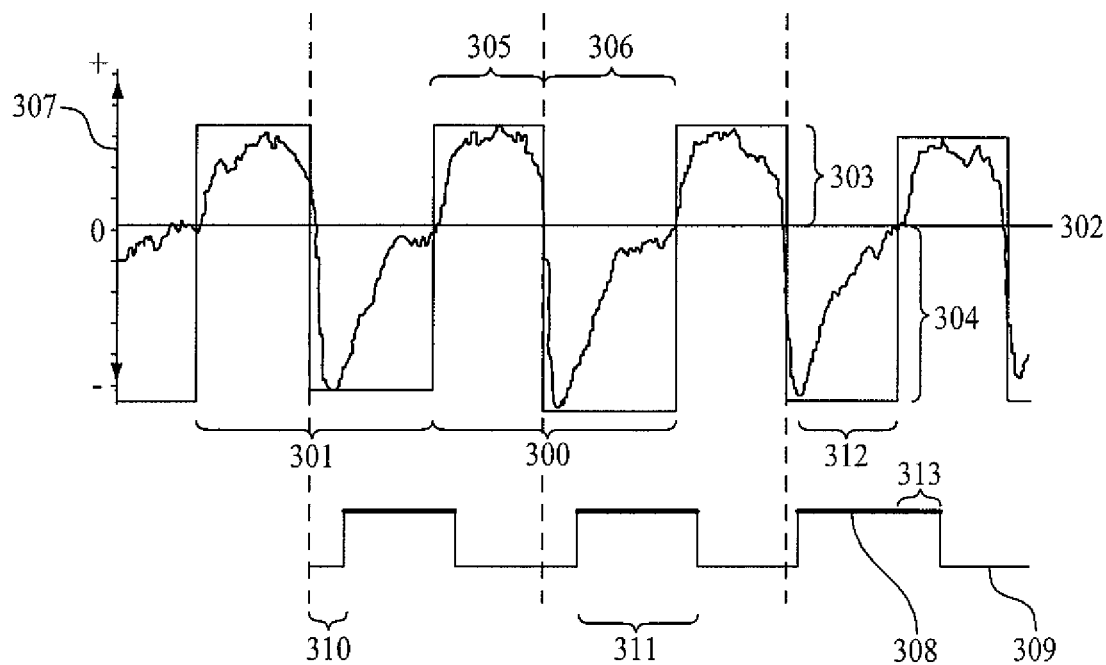
FIG. 24 is a graph illustrating the operation of a binary valve $CO_2$ rebreathing system.

FIG. 24 is a graph illustrating the operation of a binary valve that is triggered by an individual's current breath (N) 300 and recent history, for example breath (N−1) 301. Line 302 representing zero airflow into the individual differentiates inspiratory airflow 303 (positive quadrant of y-axis 307) from expiratory airflow 304 (negative quadrant). The time spent in the inspiratory phase (I} 305 is Ti, and the time spent in the expiratory phase (E) 306 is Te. In FIG. 24, the valve state is either closed 308 to atmosphere to capture exhaled gas in the breathing circuit or is open 309 to allow the $CO_2$-rich exhaled gas to be washed out of the breathing circuit. The state of the valve can be controlled by the individual's breathing pattern including but not limited to the transition from Ti to Te.

At the Ti to Te transition, the state of the valve remains unchanged for a programmed delay 310 during the initial phase of Te. After the delay, the state of the valve changes to closed 308 and stays closed for the programmed duration 311 when it then reopens. Delay 310 and duration 311 of the valve during breath (N) 300 can be fixed or variable. Varying delay 310 and/or duration 311 can be done based on the characteristics of the current breath, the Ti and Te history including but not limited to breath (N−1) 301, or an average based on a series of recent breaths. For example, delay 310 can be varies based on a percentage (e.g., 5%) of the Te of the last breath or the average of a series of breaths. Duration 311 can likewise vary and end based on a percentage (e.g., 20%) of the Ti of the last breath or the average of a series of breaths.

Another embodiment for controlling the valve is to trigger or initiate closing the valve at the maximum negative expiratory flow and keeping the valve closed through the rest of the Te 312 and into a percentage of the Ti 313.

The intra-breath valve state control shown in FIG. 24 is also regulated by a higher-level algorithm, which detects ventilatory instability. Thus, the delay and duration can be adjusted based on the breathing pattern over multiple breaths. For example, if ventilatory instability persists, then the delay can be reduced and the duration increased in iterations to help stabilize ventilation until the valve remains closed for an entire breath. The invention includes a limit to how many breaths (or total time) the valve can remain closed (without opening) to prevent an excessive retrograde volume of exhaled gas. A pulsed opening will reduce the retrograde volume of exhaled gas and then the valve can be closed again. The high-level algorithm also inactivates the intra-breath valve state control when ventilation is stable and then activates it when ventilatory instability is detected.

Figure 25:
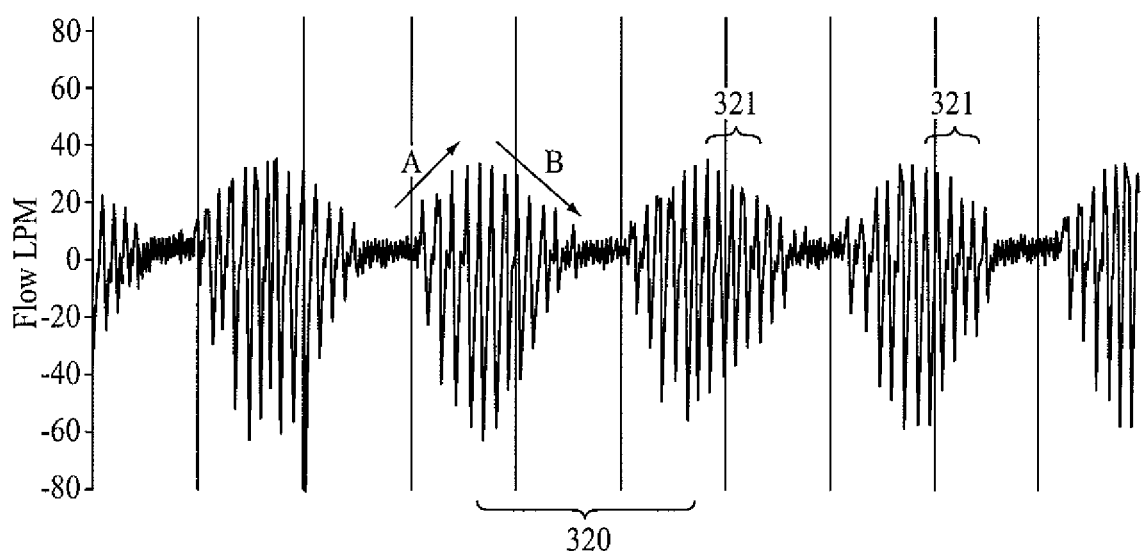
FIG. 25 is a graph of a typical CSR pattern showing the treatment timing.

FIG. 25 illustrates multiple breaths over a 5 minute period of Cheyne-Stokes respiration, which usually has a period of about 60 seconds between the peaks of hyperventilation 320. In this figure, the intra-breath valve state control is activated 321 after the peak of the crescendo arm A and remains active until the pattern reaches a target on the decrescendo arm B, when the valve state control is then inactivated.

I. Example of a Specific Ventilatory/Gas Modulation Combination Therapy

The following is a description of a specific technique for providing a therapy treatment to the patient. In this embodiment, servo-ventilation is provided to the patient to mechanically drive the patient to or near their apnea threshold (due to hyperventilation and the resulting hypocapnea). Then, controlled rebreathing of exhaled gas (or another source of carbon dioxide) is provided to increase the alveolar carbon dioxide and increase the patient's own drive to breathe. The rationale behind this approach is to improve sleep state stability by reducing the tendency to perturb an unstable system with sleep-to-wake transitions (and the associated post-arousal hyperpnea followed by decreased chemical drive to breathe).

The present invention also contemplated detecting ventilatory instability and using the result to increase pressure support (increase the delta between inspiratory and expiratory positive airway pressure to increase minute ventilation) and/or the rate at which servo-ventilated breaths are initiated (to also increase minute ventilation) until no (or intermittent) spontaneous breathing is detected and servo-ventilation has taken over breathing for the patient due to hyperventilation and the resulting hypocapnea.

This embodiment then activates $CO_2$ delivery to increase chemical drive until breathing becomes spontaneous, and then the invention uses an apparatus to capture and deliver a retrograde volume of exhaled gas (or another source of carbon dioxide) to slowly increase the partial pressure of alveolar carbon dioxide ($P_ACO_2$). This allows the $P_{CO2}$ at the chemoreceptors to rise above the apnea threshold so that spontaneous breathing can resume.

This embodiment then backs down from servo-ventilation and $CO_2$ delivery into a stable breathing state. Once breathing becomes spontaneous, the pressure support and/or servo-ventilation breath rate are reduced to reduce the minute ventilation provided by servo-ventilation. The $CO_2$ delivery to the patient is also reduced (unless ventilation becomes unstable again as indicated for example by the detection of a central apnea (or reduced chemical drive) which would indicate $CO_2$ delivery should be increased slightly while the minute ventilation provided by servo-ventilation is further reduced.

These two processes (reducing minute ventilation provided by servo-ventilation and adjusting $CO_2$ delivery) interact to allow stable breathing to resume over time without a) servo-ventilation (unless a default bi-level ventilation is desired), and b) $CO_2$ delivery to the patient. If a disturbance (arousal from sleep or body position change) causes ventilatory instability to reemerge, then the whole process beginning with the detection of ventilatory instability is reinitiated until breathing stabilizes again by the intervention proposed in this invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. System for treating ventilatory instability, comprising:
   a sensor adapted to monitor a physiological parameter of a patient;
   a processor adapted to: (i) identify a ventilatory instability experienced by the patient based on a signal provided by the sensor, (ii) determine a reference point in the patient's respiratory cycle with respect to the ventilatory instability, wherein the reference point is a peak between a crescendo phase and a decrescendo phase in a Cheyne-Stokes Respiration (CSR) cycle of the patient, and (iii) determine a start time for treatment representing a certain instance of time in the respiratory cycle, the start time being: (1) based on a delay value that is based on an estimate of delay of peripheral chemoreceptor response of the patient, and (2) aligned with the reference point;
   a therapy delivery system adapted to provide a treatment to the patient to counteract the ventilatory instability, wherein the processor causes the therapy delivery system to initiate the treatment the start time, wherein the therapy delivery system is a pressure support system, a gas modulation system, or both, and wherein the treatment includes a ventilatory therapy, a gas modulation therapy, or both.

2. The system of claim 1, wherein the processor determines a plurality of indices based on the signal provided by the sensor including a first index providing an estimate of a level of the ventilatory instability and a second index providing an estimate of a periodicity of the ventilatory instability, and wherein the processor determines a duration of the treatment based on at least the first index and the second index and causes the therapy delivery system to deliver the treatment to the patient for the determined duration beginning at the start time.

3. The system of claim 2, wherein the processor determines a) a type of therapy to be provided by the therapy delivery system, and b) a control scheme to be used in implementing the type of therapy selected.

4. The system of claim 3, wherein the control scheme is a binary control, a proportional control, an adaptive control, a rule-based control, or a learning based control.

5. The system of claim 2, wherein the plurality of indices further includes a third index providing an estimate of a flow limitation of the patient due to increased upper airway resistance.

6. The system of claim 1, wherein the therapy system includes a pressure support system that provides a bi-level pressure support or a pressure support in which an expiratory pressure is based on flow.

7. The system of claim 1, wherein the processor is adapted to determine a cycle time of the ventilatory instability, wherein the estimate of the delay of peripheral chemoreceptor response of the patient is determined based on the cycle time.

8. System for treating ventilatory instability, comprising:
   sensing means for monitoring a physiological parameter of a patient;
   processing means for: (i) identifying a ventilatory instability experienced by the patient based on a signal provided by the sensing means, (ii) determining a reference point in the patient's respiratory cycle with respect to the ventilatory instability, wherein the reference point is a peak between a crescendo phase and a decrescendo phase in a Cheyne-Stokes Respiration (CSR) cycle of the patient, and (iii) determining a start time for treatment representing a certain instance of time in the respiratory cycle, the start time being: (1) based on a delay value that is based on an estimate of delay of peripheral chemoreceptor response of the patient, and (2) aligned with the reference point;
   therapy means for providing a treatment to the patient to counteract the ventilatory instability, wherein the processing means causes the therapy delivery system to initiate the treatment at the start time, wherein the therapy means is a pressure support system, a gas modulation system, or both; and wherein the treatment includes a ventilatory therapy, a gas modulation therapy, or both.

9. The system of claim 8, wherein the processing means determines a plurality of indices based on the signal provided by the sensing means including a first index providing an estimate of a level of the ventilatory instability and a second index providing an estimate of a periodicity of the ventilatory instability, and wherein the processing means determines a duration of the treatment based on at least the first index and the second index and causes the therapy delivery system to deliver the treatment to the patient for the determined duration beginning at the start time.

10. The system of claim 9, wherein the processing means determines a) a type of therapy to be provided by the therapy means, and b) a control scheme to be used in implementing the type of therapy selected.

11. The system of claim 10, wherein the control scheme is a binary control, a proportional control, an adaptive control, a rule-based control, or an learning based control.

12. The system of claim 9, wherein the plurality of indices further includes a third index providing an estimate of a flow limitation of the patient due to increased upper airway resistance.

13. The system of claim 8, wherein the therapy means includes a pressure support system that provides a bi-level pressure support or a pressure support in which an expiratory pressure is based on flow.

14. The system of claim 8, wherein the processing means determines a cycle time of the ventilatory instability, wherein the estimate of the delay of peripheral chemoreceptor response of the patient is determined based on the cycle time.

15. Method for treating ventilatory instability, comprising:
monitoring a physiological parameter of a patient;
identifying a ventilatory instability experienced by the patient based on a signal provided by the monitored physiological parameter;
determining a reference point in the patient's respiratory cycle with respect to the ventilatory instability, wherein the reference point is a peak between a crescendo phase and a decrescendo phase in a Cheyne-Stokes Respiration (CSR) cycle of the patient;
determining a start time for treatment representing a certain instance of time in the respiratory cycle, the start time being: (1) based on a delay value that is based on an estimate of delay of peripheral chemoreceptor response of the patient, and (2) aligned with the reference point; and
providing a treatment to the patient to counteract the ventilatory instability, wherein providing the treatment includes initiating the treatment at the start time, wherein the treatment includes a ventilatory therapy, a gas modulation therapy, or both.

16. The method of claim 15, further comprising:
determining a type of therapy to be provided by the therapy means; and
determining a control scheme to be used in implementing the type of therapy selected.

17. The method of claim 15, further comprising determining a plurality of indices based on the signal including a first index providing an estimate of a level of the ventilatory instability and a second index providing an estimate of a periodicity of the ventilatory instability, and determining a duration of the treatment based on at least the first index and the second index and delivering the treatment to the patient for the determined duration beginning at the start time.

18. The method of claim 17, wherein the plurality of indices further includes a third index providing an estimate of a flow limitation of the patient due to increased upper airway resistance.

19. The method of claim 15, further comprising determining a cycle time of the ventilatory instability, wherein the estimate of the delay of peripheral chemoreceptor response of the patient is determined based on the cycle time.

* * * * *